United States Patent
Ellson et al.

(10) Patent No.: US 10,016,757 B2
(45) Date of Patent: Jul. 10, 2018

(54) SAMPLE CONTAINERS ADAPTED FOR ACOUSTIC EJECTIONS AND SAMPLE PRESERVATION AND METHODS THEREOF

(75) Inventors: Richard N. Ellson, Palo Alto, CA (US); Joseph D. Olechno, Hayward, CA (US); Robert G. Kuimelis, Palo Alto, CA (US)

(73) Assignee: Labcyte Inc., San Jose, CA (US)

( * ) Notice: Subject to any disclaimer, the term of this patent is extended or adjusted under 35 U.S.C. 154(b) by 658 days.

(21) Appl. No.: 13/457,167

(22) Filed: Apr. 26, 2012

(65) Prior Publication Data

US 2013/0109042 A1    May 2, 2013

Related U.S. Application Data

(60) Provisional application No. 61/479,985, filed on Apr. 28, 2011.

(51) Int. Cl.
*B01L 3/02* (2006.01)
*B01L 3/00* (2006.01)
*G01N 35/10* (2006.01)

(52) U.S. Cl.
CPC .............. *B01L 3/50* (2013.01); *B01L 3/0268* (2013.01); *B01L 3/50215* (2013.01); *G01N 35/10* (2013.01); *B01L 2200/0684* (2013.01); *B01L 2400/0415* (2013.01); *B01L 2400/0436* (2013.01); *G01N 2035/1041* (2013.01)

(58) Field of Classification Search
CPC .......... B01J 19/0046; B01J 2219/00596; B01J 2219/00632; B01L 3/0268; B01L 3/50; B01L 3/52

USPC ........ 436/174, 180; 422/547, 548, 549, 551, 422/552, 553
See application file for complete search history.

(56) References Cited

U.S. PATENT DOCUMENTS

| | | |
|---|---|---|
| 4,057,050 A | 11/1977 | Sarstedt |
| 4,609,017 A | 9/1986 | Coulter et al. |
| 4,875,364 A | 10/1989 | Levine et al. |
| 5,344,611 A | 9/1994 | Vogler et al. |
| 5,547,497 A | 8/1996 | Klemp et al. |
| 6,001,309 A | 12/1999 | Gamble et al. |
| 6,171,780 B1 * | 1/2001 | Pham et al. ............ 435/4 |
| 6,232,129 B1 | 5/2001 | Wiktor |

(Continued)

FOREIGN PATENT DOCUMENTS

| | | |
|---|---|---|
| JP | 11-242040 | 9/1999 |
| JP | 2002-221470 | 8/2002 |

(Continued)

OTHER PUBLICATIONS

Groner, M.D. et al., "Low-Temperature Al2O3 Atomic Layer Deposition," *Chem. Mater.*, 2004, 16(4), pp. 639-645.

(Continued)

*Primary Examiner* — Jill Warden
*Assistant Examiner* — Dwayne K Handy
(74) *Attorney, Agent, or Firm* — Faegre Baker Daniels LLP

(57) ABSTRACT

Sample container for holding and transferring a liquid sample and method thereof. The sample container includes an inlet configured to allow a liquid sample to enter a sample container, and an outlet configured to allow one or more droplets of the liquid sample to exit the sample container by one or more acoustic ejections respectively. The inlet and the outlet are in different locations.

11 Claims, 9 Drawing Sheets

(56) References Cited

U.S. PATENT DOCUMENTS

| | | | |
|---|---|---|---|
| 6,596,239 B2* | 7/2003 | Williams | B01J 19/0046 347/46 |
| 6,666,541 B2 | 12/2003 | Ellson et al. | |
| 6,849,423 B2 | 2/2005 | Mutz et al. | |
| 6,893,836 B2 | 5/2005 | Mutz et al. | |
| 6,902,705 B1* | 6/2005 | Caillat et al. | 422/552 |
| 6,938,995 B2 | 9/2005 | Mutz et al. | |
| 7,259,503 B2 | 8/2007 | Pei et al. | |
| 7,275,420 B2 | 10/2007 | Discenzo | |
| 7,595,028 B2 | 9/2009 | Minamoto et al. | |
| 7,717,544 B2 | 5/2010 | Stearns et al. | |
| 7,784,331 B2 | 8/2010 | Ellson et al. | |
| 7,899,645 B2 | 3/2011 | Qureshi et al. | |
| 7,900,505 B2 | 3/2011 | Mutz et al. | |
| 2002/0037579 A1* | 3/2002 | Ellson | B01J 19/0046 506/12 |
| 2002/0064808 A1 | 5/2002 | Mutz et al. | |
| 2002/0064809 A1 | 5/2002 | Mutz et al. | |
| 2002/0094582 A1* | 7/2002 | Williams | B01J 19/0046 436/180 |
| 2003/0085952 A1* | 5/2003 | Williams | B01L 3/5085 347/46 |
| 2005/0066711 A1 | 3/2005 | Discenzo et al. | |
| 2008/0173077 A1 | 7/2008 | Qureshi et al. | |
| 2009/0019956 A1 | 1/2009 | Ellson | |
| 2009/0123958 A1 | 5/2009 | Carmon | |
| 2009/0317884 A1 | 12/2009 | Laugharn, Jr. | |
| 2010/0140182 A1 | 6/2010 | Chapman et al. | |
| 2011/0181663 A1 | 7/2011 | Ellson | |

FOREIGN PATENT DOCUMENTS

| | | |
|---|---|---|
| JP | 2003-526081 | 9/2003 |
| JP | 2005-530140 | 10/2005 |
| JP | 2008-519280 | 6/2008 |
| JP | 2008-268078 | 11/2008 |

OTHER PUBLICATIONS

Patent Cooperation Treaty, International Search Report for corresponding PCT/US2012/035449, dated Sep. 24, 2012.
Patent Cooperation Treaty, Written Opinion of the International Searching Authority for corresponding PCT/US2012/035449, dated Sep. 24, 2012.
Wardlaw, Stephen C. and Robert A. Levine, "Quantitative Buffy Coat Analysis: A New Laboratory Tool Functioning as a Screening Complete Blood Cell Count," *JAMA*, 1983, 249(5), pp. 617-621.
Office Action dated Jan. 6, 2015 for related Chinese Patent Application No. 2012800320634, 13 pages (with English translation, 13 pages).
Supplementary Partial European Search Report for related European Patent Application No. 12776364.7, 6 pages, dated Nov. 4, 2014.
Chinese Office Action for 201280032063.4 dated Sep. 25, 2015 (3 pages).
Japanese Office Action dated Mar. 29, 2016 for JP 2014-508599 (11 pages).
Chinese Office Action dated May 10, 2016 for CN 20120032063.4 (9 pages).
Office action for Chinese patent application 2012800320634 dated Feb. 14, 2017, with English language translation (7 pages).
Canadian Intellectual Property Office, Office Action dated Feb. 15, 2018, for Application No. 2,834,398.
Korean Intellectual Property Office, Office Action dated Feb. 12, 2018, for Application No. 10-2013-7031125.

* cited by examiner

SAMPLE CONTAINERS ADAPTED FOR ACOUSTIC EJECTIONS AND SAMPLE PRESERVATION AND METHODS THEREOF

1. CROSS-REFERENCES TO RELATED APPLICATIONS

This application claims priority to U.S. Provisional Patent Application No. 61/479,985, filed Apr. 28, 2011, commonly assigned, incorporated by reference herein for all purposes.

2. BACKGROUND OF THE INVENTION

The present invention is directed to sample handling. More particularly, certain embodiments of the present invention provide sample containers adapted for acoustic ejections and analyses and methods thereof. Merely by way of example, the invention has been applied to biological samples. But it would be recognized that the invention has a much broader range of applicability, such as preservation of liquid sample within a sample container.

It is often desired to take a biological sample (e.g., a human blood sample) contained in an individual sample holder and to transfer it to one or more well plates or other objects appropriate for carrying out reactions with the biological sample (e.g., onto test strips). Usually, a single biological sample (e.g., a single human blood sample) may be divided up among a number of these downstream containers in order to be subjected to a wide variety of different tests. Many biological samples also include a plurality of components that may be separable and preferentially subjected to tests as separable components. For example, blood samples in tubes are commonly centrifuged and stratified into multiple layers, with plasma located at the top, red blood cells at the bottom and other blood components in between. Furthermore, many biological samples may degrade during storage, so it is desirable to adapt the sample holder to create an environment to preserve the biological samples.

Some important considerations for the handling of biological samples include: ability to obtain a number of measurements from a single extracted sample (e.g., a single blood draw); generating no waste in the sample transfer; providing a proportionate amount of fluid, particulates and cells with a transfer and overcoming challenges in achieving such transfer at small volumes; enabling various types of diagnostics that can benefit from consistent deliveries of small-volume samples; elimination of manual pipetting and associated wastes and interactions with tips, sharps, capillaries, and needles, in order to improve lab safety; reducing the training needed for lab technicians to achieve high-quality small-volume sample transfers; and/or using the same container for blood collection, storage and as a source for transfer.

Acoustic ejection has been known for a number of years as a way of performing transfers of biological samples. For example, in a typical setup for acoustic ejection, a piezoelectric transducer is driven by a waveform chosen by a controller and in response generates acoustic energy. The acoustic energy often is focused by an acoustic lens, and coupled to a reservoir containing fluid through an acoustic coupling medium (e.g., water). If the focused energy has a focal point inside a fluid in the reservoir and close to a free surface of that fluid, a droplet may be ejected. Droplet size and velocity can be controlled by the chosen waveform as mentioned above.

In some embodiments, the transducer is movable in one or more directions (e.g., in the "z direction") that is roughly perpendicular to the free surface of the fluid. The movement can take place under the control of the controller. Some acoustic instruments for high-throughput use rely on an active control of the transducer position relative to the reservoir and address the multiplicity of wells in microplates. Often, the adjustment of the transducer position involves sending a motion command to a motion controller which then initiates movement in one or more directions (e.g., along one or more axes). For example, motion in the horizontal plane (e.g., in the "x direction" and/or in the "y direction") aligns the transducer with the selected reservoir, and motion in the vertical direction (e.g., in the "z direction") is used both to audit the reservoir and to focus for droplet transfer. In another example, positioning of the transducer to achieve the proper focus for droplet ejections can be responsive to data collected from an acoustic audit. Additionally, U.S. Pat. Nos. 6,938,995 and 7,900,505 are incorporated by reference herein for all purposes. When the motion is complete, the controller can notify the system that the transducer and the reservoir are now in the proper position for the next step in the process. In some contexts, it is desirable to accomplish acoustic ejections of selected regions within a single sample that have been separated, and such ejections may be facilitated by motion of the transducer in the horizontal plane. Moreover, U.S. Pat. No. 6,666,541 is incorporated by reference herein for all purposes.

Beyond transfer of simple fluid, focused acoustic energy recently has been used in applications involving biological matters such as living cells. For example, focused acoustic radiation has been used to manipulate and sort cells. U.S. Patent Application Publication Nos. 2002/0064808 and 2002/0064809 and U.S. Pat. Nos. 6,893,836 and 6,849,423 are incorporated by reference herein for all purposes. In another example, containers for sample collection are also widely used. The conventional containers (e.g., containers used in extraction and/or storage of samples) usually are not adapted for use in acoustic transfer.

Additionally, methods for separation of samples within sample containers are well known. For example, blood samples are commonly centrifuged to separate components into layers. Often, such separation is performed in order to access a particular component for analysis. In another example, a stratum from a normal blood sample, from top to bottom, includes plasma, platelets, non-granulocytes (e.g., lymphocytes and monocytes), granulocytes (e.g., basophils, eosinophils, and neutrophils) and then red blood cells (e.g., reticulocytes and erythrocytes).

Moreover, methods for improving homogeneity of samples within sample containers are also well known. For example, blood samples are commonly inverted manually (e.g., for twenty times) to agitate the samples and re-suspend the cells. In another example, automated systems for sample handling can perform a similar function by rocking and/or rotating sample containers.

Additionally, methods to prevent degradation of samples are well known. Blood samples often are collected into containers that already have reagents inside to preserve the samples. For example, ethylenediaminetetraacetic acid (EDTA), a strong chelator of metal ions, is added to eliminate or reduce the activity of metalloproteases in solution because such activity can degrade peptide biomarkers. Additionally, EDTA can also prevent or reduce coagulation of the blood samples by binding to calcium ions and preventing the coagulation cascade from occurring. In another example, sodium fluoride is added to sample containers (e.g., blood collection tubes) in order to stop degradation of glucose in the blood samples. In yet another example, these additives (e.g., EDTA and sodium fluoride) are present in the sample containers as a solution, a dried residue and/or a non-covalent coating (e.g., spray-coating) on interior surfaces of the containers.

Often, these additives can become integral to the blood samples after the samples enter the containers, and these additives may have a negative impact on downstream assays. Therefore, blood samples often are collected in multiple sample containers (e.g., tubes) that contain specific additives that are compatible with respective downstream analyses.

Furthermore, the sample containers (e.g., blood collection tubes) with additives often require that the blood samples and the additives be mixed through partial or complete inversion of the containers once the containers are filled with blood samples. The efficacy of mixing by inversion or semi-inversion usually is dramatically decreased as the volume of the blood sample and the size of the sample container are reduced. Efficacy loss can be due to inability of the container motion to be strong enough to overcome the adhesion of the sample to the container surfaces, or inability of the change of container in orientation with respect to gravity to be strong enough to overcome the adhesion of the sample to the container surfaces. The reduction in efficacy may lead to a delay in the role of the additives as preservatives of certain biological markers.

Researchers also have shown that endogenous enzymes (e.g., proteases and peptidases) in blood samples can degrade and destroy peptide and protein constituents, which are important biomarkers of the blood samples. Hence some blood collection tubes have been introduced with additives that can inhibit various proteases.

Therefore, there is a need for acoustic ejection systems and sample containers that can in combination significantly simplify handling of biological samples and are amenable to miniaturization.

3. BRIEF SUMMARY OF THE INVENTION

The present invention is directed to sample handling. More particularly, certain embodiments of the present invention provide sample containers adapted for acoustic ejections and analyses and methods thereof. Merely by way of example, the invention has been applied to biological samples. But it would be recognized that the invention has a much broader range of applicability, such as preservation of liquid sample within a sample container.

According to one embodiment, a sample container for holding and transferring a liquid sample includes an inlet configured to allow a liquid sample to enter a sample container, and an outlet configured to allow one or more droplets of the liquid sample to exit the sample container by one or more acoustic ejections respectively. The inlet and the outlet are in different locations.

According to another embodiment, a method for holding and transferring a liquid sample includes transferring a liquid sample into a sample container through an inlet, and acoustically ejecting one or more droplets of the liquid sample out of the sample container through an outlet. The inlet and the outlet are in different locations.

According to yet another embodiment, a method for holding a liquid sample includes transferring a liquid sample into a sample container, adding one or more materials to one or more interior surfaces of the sample container, and binding one or more components of the liquid sample to the one or more materials on the one or more interior surfaces of the sample container.

Depending upon embodiment, one or more benefits may be achieved. These benefits and various additional objects, features and advantages of the present invention can be fully appreciated with reference to the detailed description and accompanying drawings that follow.

4. BRIEF DESCRIPTION OF THE DRAWINGS

FIGS. 1(A) and (B) are simplified diagrams showing a sample container adapted for acoustic ejection and analysis according to an embodiment of the present invention.

Figure 4A:
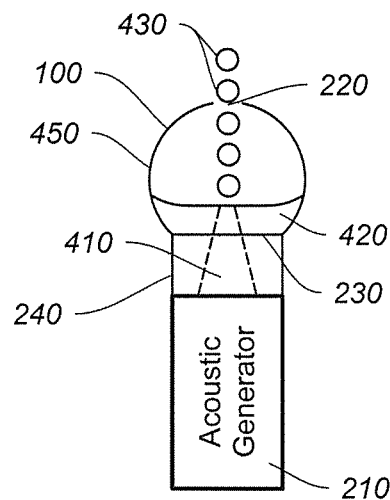

FIGS. 4(A) and (B) are simplified diagrams showing one or more droplets of the liquid sample being ejected from the sample container by the acoustic generator according to an embodiment of the present invention.

Figures 5A, 5B:
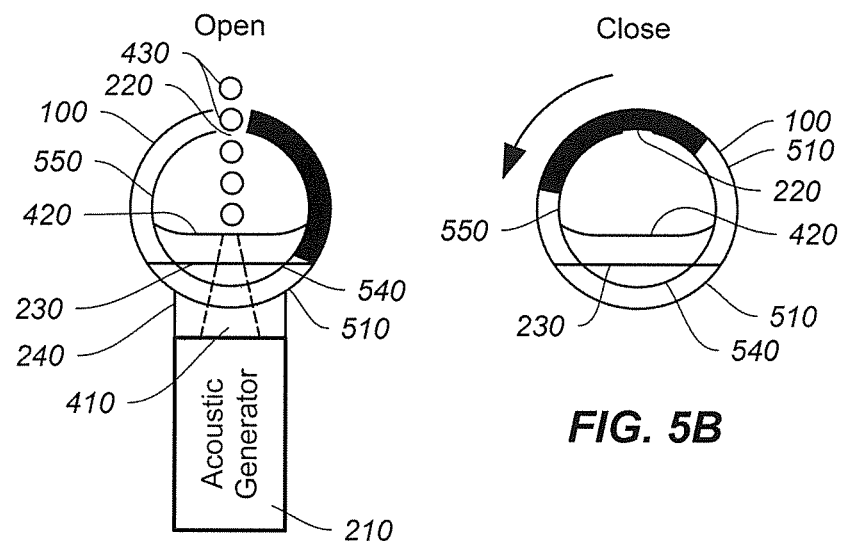

FIGS. 5(A) and (B) are simplified diagrams showing the sample container together with the acoustic generator for acoustic ejection and/or analysis according to another embodiment of the present invention.

Figure 6:
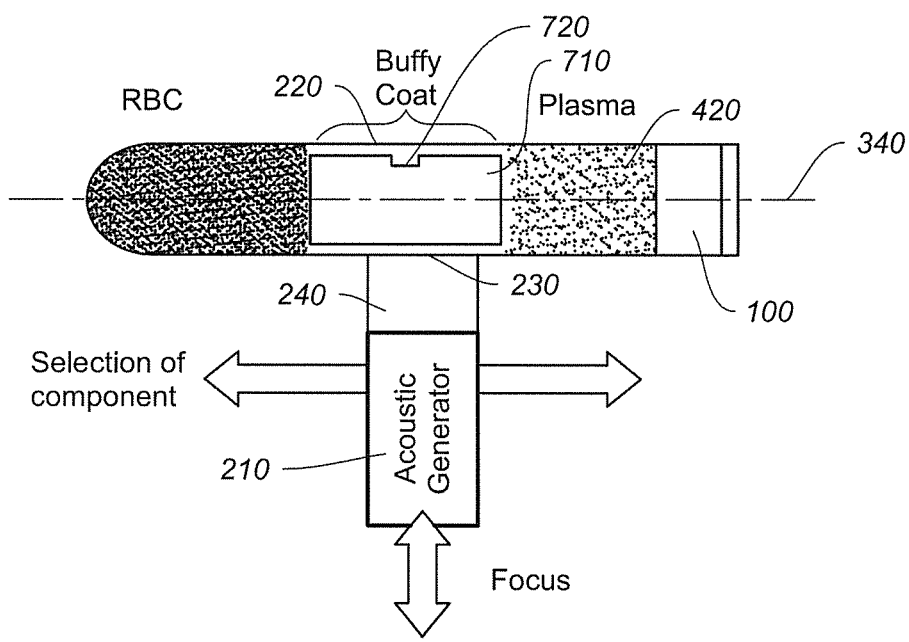

FIG. 6 is a simplified diagram showing separation of components of the liquid sample using a float in the sample container and selection of one or more components for acoustic ejection according to one embodiment of the present invention.

Figure 7A:
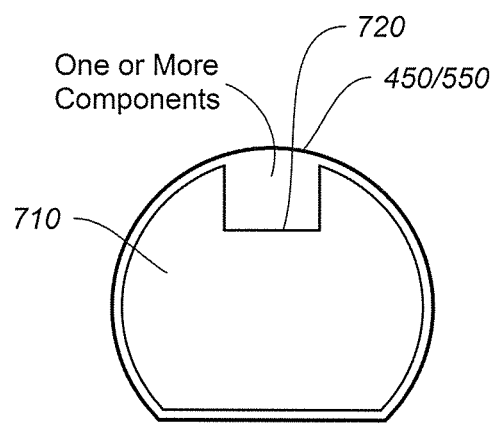

FIG. 7(A) is a simplified diagram showing a cross-section of the float used in the sample container according to an embodiment of the present invention.

Figure 7B:
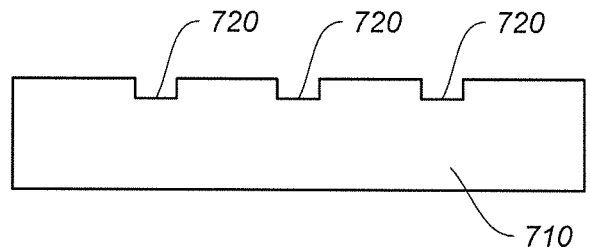

FIG. 7(B) is a simplified diagram showing another cross-section of the float used in the sample container according to another embodiment of the present invention.

Figure 8:
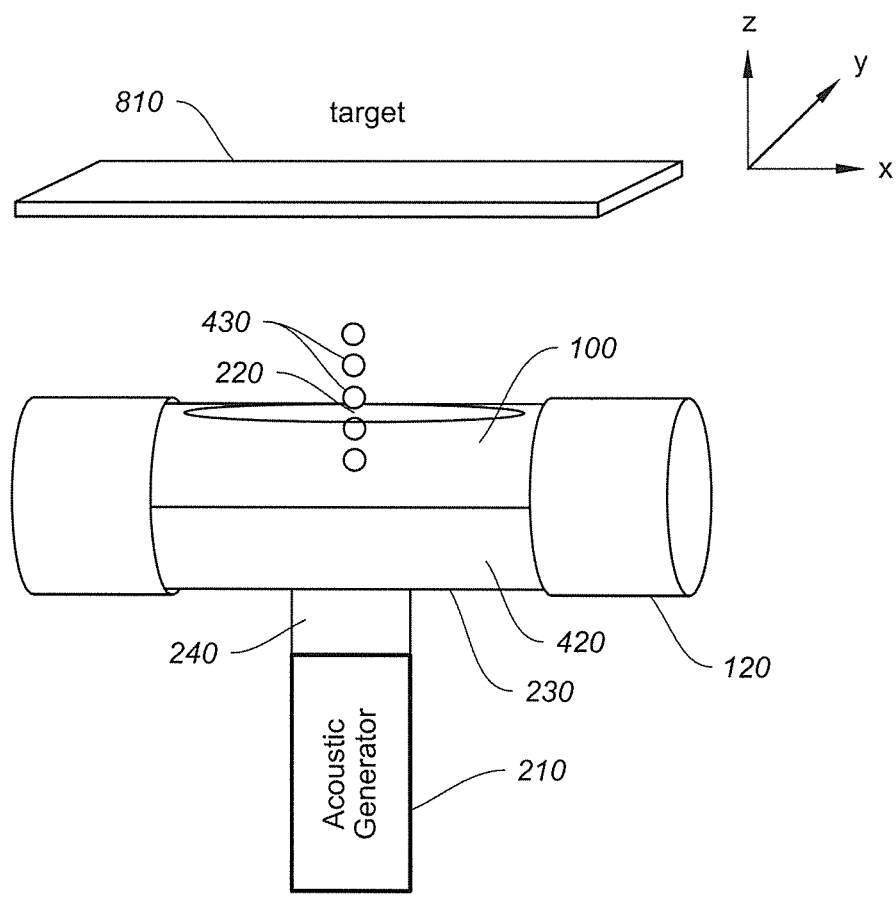

FIG. 8 is a simplified diagram showing one or more droplets of the liquid sample being ejected from the sample container by the acoustic generator to a target according to an embodiment of the present invention.

Figure 9:
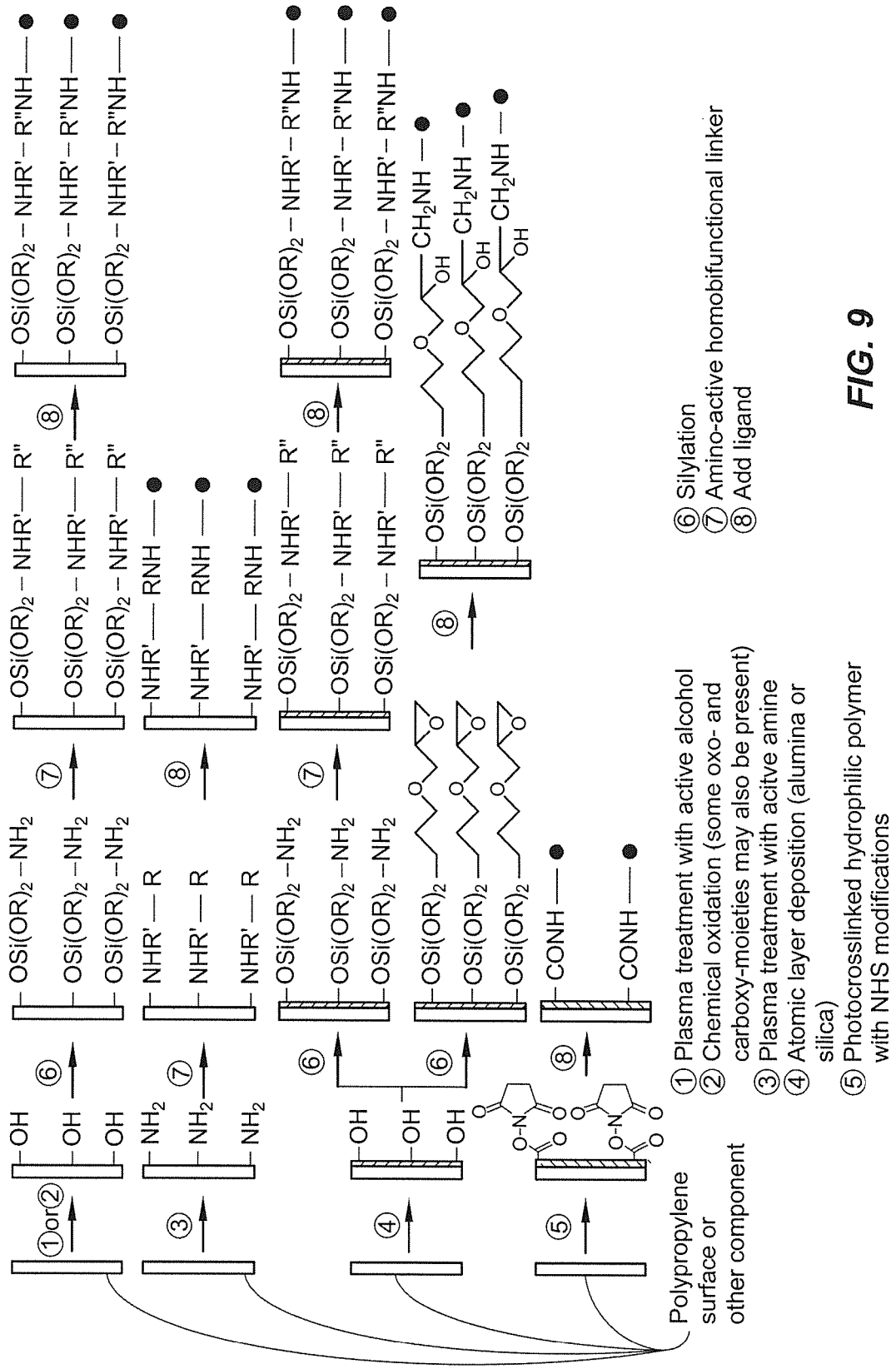

FIG. 9 is a simplified diagram showing various combinations of surface treatment processes for one or more interior surfaces of the sample container and/or one or more other components integral to the interior of the container according to certain embodiments of the present invention.

5. DETAILED DESCRIPTION OF THE INVENTION

The present invention is directed to sample handling. More particularly, certain embodiments of the present invention provide sample containers adapted for acoustic ejections and analyses and methods thereof. Merely by way of example, the invention has been applied to biological samples. But it would be recognized that the invention has a much broader range of applicability, such as preservation of liquid sample within a sample container.

With respect to various embodiments of the present invention, it is to be understood that this invention is not limited to specific solvents, materials, and/or device structures, as such may vary. It is also to be understood that the terminology used herein is for the purpose of describing particular embodiments only, and is not intended to be limiting.

According to some embodiments, the singular forms "a," "an," and "the" include both singular and plural referents unless the context clearly dictates otherwise. For example, reference to "a fluid" includes a plurality of fluids as well as a single fluid. In another example, reference to "a temperature" includes a plurality of temperatures as well as a single temperature.

According to certain embodiments, where a range of values is provided, it is intended that each intervening value between the upper limit and the lower limit of that range and any other stated or intervening value in that stated range is encompassed within the disclosure. For example, if a range of 1 µm to 8 µm is stated, it is intended that at least 2 µm, 3 µm, 4 µm, 5 µm, 6 µm, and 7 µm are also disclosed, as well as the range of values that are greater than or equal to 1 µm and less than or equal to 8 µm.

According to some embodiments, reference is sometimes made to "horizontal" or "vertical" in terms of acoustic ejection configuration where a fluid is in a sample container and has a free surface which is approximately horizontal (e.g., approximately perpendicular to the direction of the earth's gravity).

As discussed above, there is a need for acoustic ejection systems and sample containers which in combination can simplify the full life cycle of processing biological samples (e.g., collecting, transferring, preserving, and/or analyzing biological samples) by using acoustic ejection and/or acoustic analysis.

For example, the conventional collection containers (e.g., containers used in extraction and/or storage of samples) usually are not adapted for use in acoustic transfer. Often, these conventional containers are tubular in geometry and have rounded bottoms to facilitate complete transfer out of the tube by pipettes. Curved container surfaces can alter the acoustic beam and pose additional challenges to aligning the beam with the container, analyzing the fluid in the container, and focusing the beam at the sample surface to enable acoustic ejection. Also, the conventional containers usually are not fabricated or labeled to facilitate uniform propagation of the acoustic beam towards a free surface of the sample such that a droplet can be ejected out of the container. For example, certain conventional containers are roughly cylindrical tubes that have been molded in such a manner as to having a small nub or molding artifact directly opposite their open tops in the middle of the tube bottoms (e.g., where the plastic entered the mold during the manufacturing process). Such small nub or molding artifact can disrupt uniformity of sound entering at this location. In another example, some conventional tubes, in addition to having curved exterior walls, have exterior labels that are made of paper consisting of fibers that can scatter sound, or have adhesive layers containing air gaps that can disrupt uniform transfer of acoustic energy.

Hence, there is a need, in particular, for sample containers to provide one or more acoustic paths that are amenable to uniform and efficient acoustic propagation from outside the container to surface of the sample inside the container according to some embodiments. For example, the one or more acoustic paths are also in line with droplets ejected from the surface towards an open or openable outlet. In another example, the one or more acoustic paths are free of scattering and/or non-focusing objects (e.g., bubbles), and/or have low surface roughness and/or low attenuation.

Figure 1A:
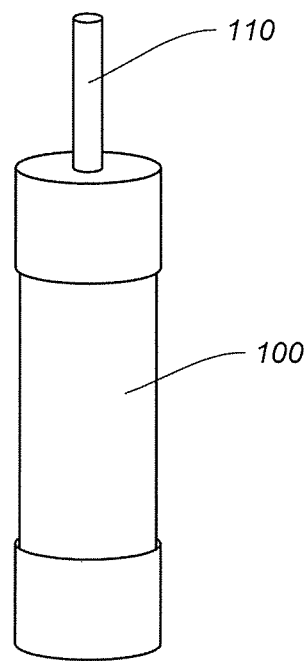

FIGS. 1(A) and (B) are simplified diagrams showing a sample container adapted for acoustic ejection and analysis according to an embodiment of the present invention. This diagram is merely an example, which should not unduly limit the scope of the claims. One of ordinary skill in the art would recognize many variations, alternatives, and modifications.

As shown in FIG. 1(A), the sample container 100 (e.g., a tube) includes an inlet 110 for a liquid sample (e.g., a biological sample) to enter the sample container. In one embodiment, the inlet 110 is associated and/or integral with an extraction device (e.g., a lance) for the liquid sample. For example, the inlet 110 and the extraction device are separable. In another embodiment, the inlet 110 is not associated or integral with any extraction device (e.g., a lance) for the liquid sample.

According to one embodiment, the liquid sample is stored in the sample container 100 that is placed in an upright orientation and/or a vertical orientation with the inlet 110 at the top. For example, one or more droplets of the liquid sample are acoustically ejected out of the sample container through the inlet 110 at the top. U.S. Patent Application Publication Nos. 2009/0019956 and 2011/0181663 are incorporated by reference herein for all purposes.

Figure 1B:
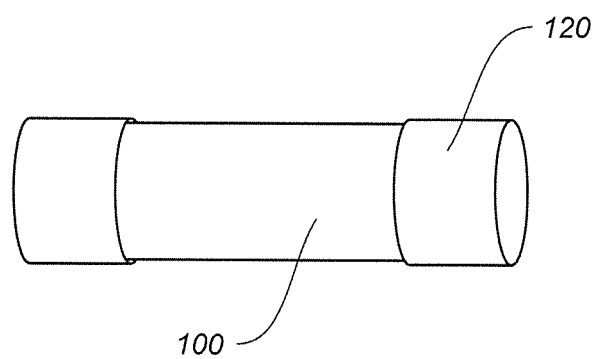

According to another embodiment, as shown in FIG. 1(B), the inlet 110 is replaced by a cap 120 after the liquid sample has entered the sample container 100; therefore, the cap 120 becomes a part of the sample container 100, which no longer includes the inlet 110. For example, using the cap 120, the liquid sample is stored in the sample container 100 that is placed in sideways and/or in a horizontal orientation.

Figure 2:
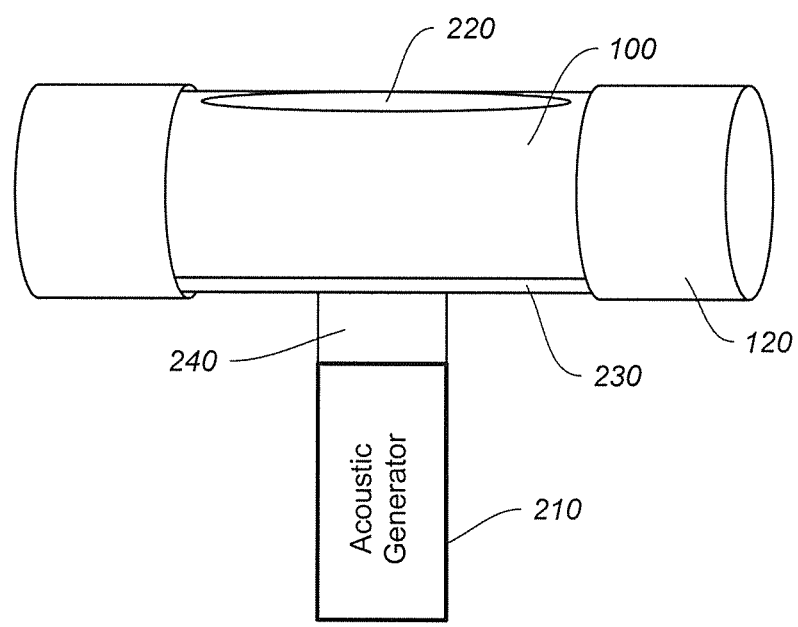
FIG. 2 is a simplified diagram showing the sample container together with an acoustic generator for acoustic ejection and/or analysis according to an embodiment of the present invention.

FIG. 2 is a simplified diagram showing the sample container 100 together with an acoustic generator for acoustic ejection and/or analysis according to an embodiment of the present invention. This diagram is merely an example, which should not unduly limit the scope of the claims. One of ordinary skill in the art would recognize many variations, alternatives, and modifications.

As shown in FIG. 2, an acoustic generator 210 (e.g., an acoustic transducer) is situated below the sample container 100. For example, the sample container 100 is placed in a horizontal orientation and includes an outlet 220. In another example, the acoustic generator 210 is located opposite to the outlet 220 from which droplets of a liquid sample (e.g., a biological sample) can be emitted out of the sample container 100.

In one embodiment, the liquid sample is situated within the sample container 100 on a bottom surface 230 of the sample container 100 above an acoustic coupling material 240. For example, the acoustic coupling material 240 is placed between the bottom surface 230 and the acoustic generator 210. In another example, the bottom surface 230 is flat. In yet another example, the bottom surface 230 is acoustically uniform between different locations of the bottom surface 230. In yet another example, the outlet 220 is opposite to the bottom surface 230, which also serves as a side surface of the sample container 100.

In another embodiment, the outlet 220 is open (e.g., unsealed) or closed (e.g., sealed). For example, the outlet 220 is closed for storage of the liquid sample within the sample container 100. In another example, the outlet 220 is open for ejection of droplets of the liquid sample out of the sample container 100.

According to one embodiment, the outlet 220 is sealed or unsealed by one or more mechanical methods such as manual application or removal of a stopper, an external cover ring, and/or an adhesive seal. According to another embodiment, the outlet 220 is sealed or unsealed by one or more electromechanical methods such as automated movements of a stopper, an external cover ring, and/or an adhesive seal. For example, the electromechanical methods use a robot and/or a solenoid. According to yet another embodiment, the outlet 200 is opened and closed automatically by one or more materials that are integral to the sample container 100 such as the one or more materials that can be activated by an electrical signal. For example, the outlet 200 includes one or more apertures formed by electro-active polymers.

Figure 3:
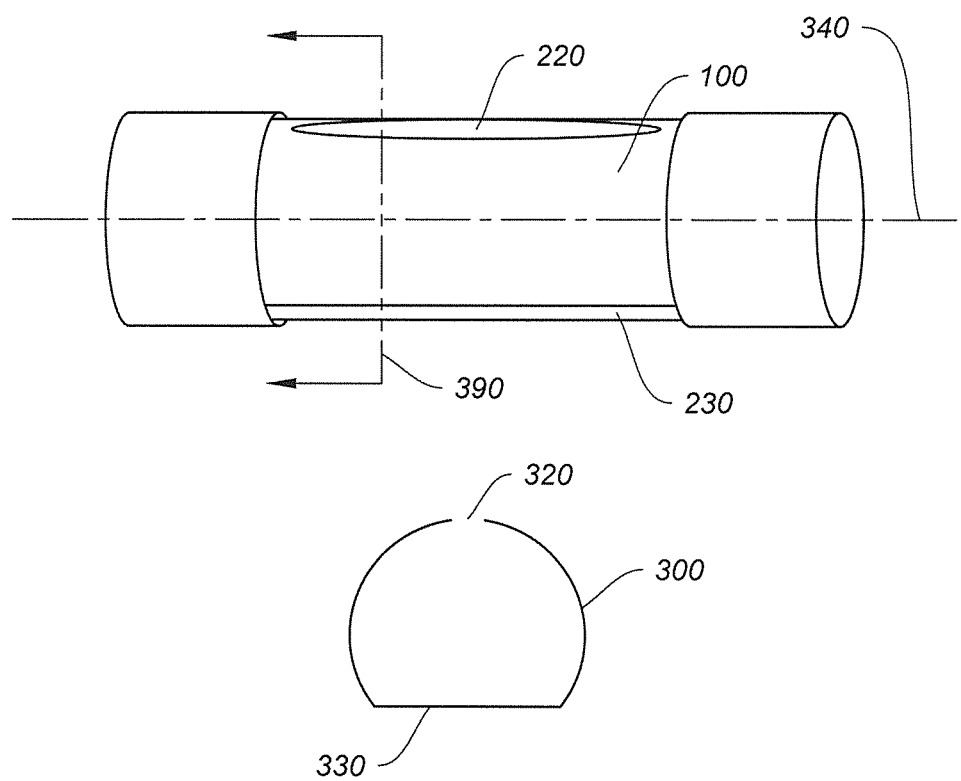
FIG. 3 is a simplified diagram showing the sample container and a cross-section of the sample container adapted for acoustic ejection and analysis according to an embodiment of the present invention.

FIG. 3 is a simplified diagram showing the sample container 100 and a cross-section of the sample container 100 adapted for acoustic ejection and analysis according to an embodiment of the present invention. This diagram is merely an example, which should not unduly limit the scope of the claims. One of ordinary skill in the art would recognize many variations, alternatives, and modifications.

As discussed above, the sample container 100 includes, for example, the outlet 220 and the bottom surface 230. As shown in FIG. 3, a cross-section 300 of the sample container 100 is taken along a plane 390, which is perpendicular to an axis 340 of the sample container 100. In one embodiment, the cross-section 300 includes an outlet section 320 and a bottom section 330. For example, the outlet section 320 is a cross-section of the outlet 220. In another example, the bottom section 330 is a cross-section of the bottom surface 230.

Returning to FIG. 2, the acoustic coupling material 240 includes an acoustic coupling medium (e.g., a coupling fluid) according to one embodiment. In another embodiment, there is also a flexible membrane between the acoustic coupling medium and the sample container 240. For example, such membrane is applied to the bottom surface 230 of the sample container 100 without trapping bubbles.

In one embodiment, the coupling membrane is made of a "wet" material, such as a hydrogel-like substance and/or any other material that is similar to a contact lens. For example, the "wet" material, like a contact lens, can provide focusing of acoustic energy generated by the acoustic generator 210. In another example, the "wet" material serves as a defocusing material to increase the focal length of the acoustic energy (e.g., in the form of an acoustic beam).

In another embodiment, the coupling membrane is perforated. For example, the perforated membrane includes holes that are small relative to the wavelength of the acoustic energy generated by the acoustic generator 210. In another example, the perforated membrane includes holes that are oriented symmetrically about the center of the acoustic generator 210 so as not to distort the propagation of the acoustic energy generated by the acoustic generator 210. In yet another embodiment, the focusing of acoustic energy is performed by one or more separate components (e.g., by the "wet" membrane and/or a lens integral to the acoustic generator 210).

As briefly mentioned above, it is desirable that the acoustic path from the acoustic generator 210 (e.g., an acoustic transducer) to the fluid meniscus inside the sample holder 100 be substantially free of bubbles. For example, the bubbles may scatter the acoustic energy (e.g., in the form of acoustic beam), so it is desirable to eliminate all bubbles, even though bubbles that are tiny (with respect to the acoustic beam) cause fewer problems than those which are on the order of the acoustic wavelength. In another example, an arrangement which is helpful in eliminating bubbles between the acoustic generator 210 and the sample container 100 is to have bubble-free water rising from around the acoustic generator 210 and flowing toward the sample container 100. In yet another example, the elimination of bubbles in the acoustic path within the sample container 100 is also helpful. According to one embodiment, one or more methods can be used for reducing the likelihood for bubbles to exist in the liquid sample within the sample container 100. For example, such methods include centrifugation. In another example, such methods include making inner surfaces of the sample container 100 easily wetted by the liquid sample (e.g., by rolling, rocking and/or inverting the sample container). According to another embodiment, bubbles are detected by acoustics within the liquid sample, and then removed from the liquid sample.

FIGS. 4(A) and (B) are simplified diagrams showing one or more droplets of the liquid sample being ejected from the sample container 100 by the acoustic generator 210 according to an embodiment of the present invention. These diagrams are merely examples, which should not unduly limit the scope of the claims. One of ordinary skill in the art would recognize many variations, alternatives, and modifications.

As shown in FIGS. 4(A) and (B), the sample container 100 (e.g., a sample tube) is placed in the horizontal orientation. In one embodiment, an acoustic beam 410 generated by the acoustic generator 210 enters the sample container 100 through the acoustic coupling material 240 and focuses near the meniscus of a liquid sample 420 within the sample container 100. In another embodiment, one or more droplets 430 of the liquid sample 420 are ejected by the acoustic beam 410 out of the sample holder 100 through the outlet 220 if the outlet 220 is open (e.g., unsealed).

As shown in FIG. 4(A), the liquid sample 420 is situated within the sample container 100 on the bottom surface 230, which also serves as an outer surface section of the sample container 100. In one embodiment, the sample container 100 also has another outer surface section 450, which in combination with the bottom surface 230 forms an outer surface of the sample container 100 in at least one cross-section. For example, the outlet 220 is an outlet through the outer surface section 450. In another example, the bottom surface 230 is flat. In yet another example, the acoustic coupling material 240 is placed between the bottom surface 230 and the acoustic generator 210.

Figure 4B:
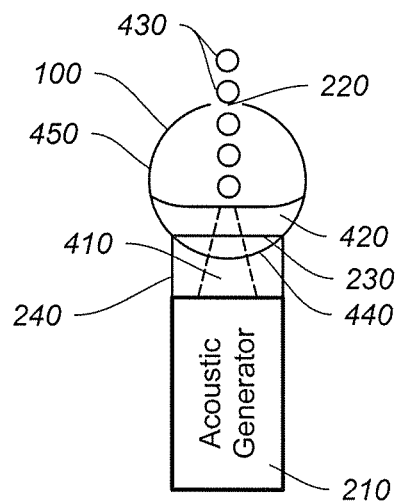

As shown in FIG. 4(B), even though the liquid sample 420 is situated within the sample container 100 on the bottom surface 230, the bottom surface 230 does not serve as an outer surface section of the sample container 100. For example, the bottom surface 230 is flat. In another example, the bottom surface 230 is covered by an outer surface section 440. According to one embodiment, the acoustic coupling material 240 is placed between the outer surface section 440 and the acoustic generator 210. According to another embodiment, the sample container 100 has a circular outer surface in at least one cross-section. For example, the circular outer surface includes the outer surface section 440 and the outer surface section 450. In another example, the outlet 220 is an outlet through the outer surface section 450.

As discussed above and further emphasized here, FIGS. 2, 3, 4(A), and 4(B) are merely examples, which should not unduly limit the scope of the claims. One of ordinary skill in the art would recognize many variations, alternatives, and modifications. For example, the outer surface sections 440 and 450 are covered by another outer surface, so that the outer surface sections 440 and 450 are not exposed. In another example, another outer surface can be rotated to close (e.g., seal) and open (e.g., unseal) the outlet 220.

FIGS. 5(A) and (B) are simplified diagrams showing the sample container 100 together with the acoustic generator 210 for acoustic ejection and/or analysis according to another embodiment of the present invention. These diagrams are merely examples, which should not unduly limit the scope of the claims. One of ordinary skill in the art would recognize many variations, alternatives, and modifications.

As shown in FIG. 5(A), the acoustic generator 210 (e.g., an acoustic transducer) is situated below the sample container 100. For example, the sample container 100 is placed in the horizontal orientation and includes the outlet 220. In another example, the acoustic generator 210 is located opposite to the outlet 220 from which the one or more droplets 430 of the liquid sample 420 (e.g., a biological sample) can be emitted out of the sample container 100 if the outlet 220 is open (e.g., unsealed).

According to one embodiment, even though the liquid sample 420 is situated within the sample container 100 on the bottom surface 230, the bottom surface 230 is an inner surface section of the sample container 100. For example, the bottom surface 230 is flat. In another example, the bottom surface 230 is covered by a surface section 540. In yet another example, the surface section 540 and another surface section 550 form a circular surface in at least one cross-section. In yet another example, the outlet 220 is an outlet through the surface section 550.

According to another embodiment, the surface sections 540 and 550 are covered by an outer surface 510. For example, the acoustic coupling material 240 is placed between the outer surface 510 and the acoustic generator 210. In another example, the outer surface 510 is rotated to open (e.g., unseal) the outlet 220 as shown in FIG. 5(A), and to close (e.g., seal) the outlet 220 as shown in FIG. 5(B).

In one embodiment, the sample holder 100 uses an integral unsealing/sealing method (e.g., as shown in FIG. 5(A) in the open position and as shown in FIG. 5(B) in the closed position). For example, a rotation of the inner portion (e.g., the surface sections 540 and 550) with respect to the outer portion (e.g., the outer surface 510) brings a sealing material in contact with the opening (e.g., the outlet 220), causing the sample container 100 to change from the open position to the closed position.

In another embodiment, as shown in FIGS. 5(A) and (B), the volumes enclosed by the outer portion (e.g., the outer surface 510) and the inner portion (e.g., the surface sections 540 and 550) are within 10% of each other. In yet another embodiment, it is desirable to have the outer portion (e.g., the outer surface 510) selected for ease of manual or automated handling, while the inner portion (e.g., the surface sections 540 and 550) is scaled to reduce the total volume enclosed, so that the volumes enclosed by the inner portion and the outer portion differ by more than 80%. In yet another embodiment, to further reduce the volume enclosed by the inner portion (e.g., the surface sections 540 and 550), the inner portion does not extend through the entire length of the outer portion (e.g., alone the axis 340 of the sample container 100). For example, the inner portion (e.g., the surface sections 540 and 550) extends no more than 10% of the outer portion (e.g., the outer surface 510) alone the axis 340 of the sample container 100.

Returning to FIG. 2, the acoustic generator 210 is moved relative to the sample container 100 to select another region from which to eject one or more droplets of the liquid sample (e.g., the liquid sample 420) out of the sample container 100 according to one embodiment. For example, another region corresponds to the location of another component of the liquid sample 420 in the sample container 100, such as a layer from the stratification of the liquid sample 420.

FIG. 6 is a simplified diagram showing separation of components of the liquid sample 420 using a float in the sample container 100 and selection of one or more components for acoustic ejection according to one embodiment of the present invention. This diagram is merely an example, which should not unduly limit the scope of the claims. One of ordinary skill in the art would recognize many variations, alternatives, and modifications.

For example, certain components of the liquid sample 420 (e.g., a human blood sample) are separated by segregation in the presence of a float 710 (e.g., a float of specific gravity that is similar to the selected one or more components within the liquid sample 420). In another example, the float 710 includes one or more collection regions 720 (e.g., one or more depression regions). In yet another example, the float 710 is comprised of at least one or more materials such as a glass. In yet another example, the float 710 is comprised of at least one or more materials such as a polymer (e.g., polypropylene, polyethylene, polystyrene, polycarbonate, and/or COC).

As shown in FIG. 6, the selection of one or more components is achieved by moving the acoustic generator 210 (e.g., an acoustic transducer) in the horizontal plane (e.g., in the "x direction" and/or in the "y direction"). Also as shown in FIG. 6, focusing of the acoustic energy (e.g., focusing of the acoustic beam 410) is achieved by moving the acoustic generator 210 (e.g., the acoustic transducer) in the vertical direction (e.g., in the "z direction").

According to some embodiments, one or more methods that separate components of the liquid sample 420 and stratify the components, such as centrifugation of blood, can be used in order to transfer one or more components of the liquid sample 420 from the sample holder 100 by acoustic energy. According to certain embodiments, the centrifugation is used to separate blood components and enables regions of less prevalent components to be sequestered within the collection region 720 of the float 710 (e.g., a depression region of a float of similar specific gravity).

In one embodiment, the presence of one or more floats 710 within the sample container 100 is provided to promote isolation of specific components of the liquid sample 420 and facilitate acoustic transfer. For example, if there is more than one float, the density of the floats 710 is selected to correspond to components of the liquid sample 420 to be extracted as the floats 710 would stratify with the matching density material. In another example, the positions of the floats 710 as well as the locations of the components are determined by acoustic measurement and detection of the difference in acoustic properties of these component materials (e.g., impedance and/or acoustic attenuation). U.S. Pat. Nos. 6,938,995 and 7,784,331 are incorporated by reference herein for all purposes.

In another embodiment, it would be preferable to select the float material to enable the float 710 to be acoustically distinguishable from the fluid (e.g., from one or more component materials) of the same or similar density surrounding the float 710. For example, since the acoustic impedance is the product of density and sound speed, the float material is chosen with the same density as the surrounding fluid but with a different sound speed, so there would be a mismatch in the acoustic impedance between the float 710 and the surrounding fluid.

FIG. 7(A) is a simplified diagram showing a cross-section of the float 710 used in the sample container 100 according to an embodiment of the present invention. This diagram is merely an example, which should not unduly limit the scope of the claims. One of ordinary skill in the art would recognize many variations, alternatives, and modifications.

As shown in FIG. 7(A), a cross-section of the float 710 (e.g., a "free-floating" float) is taken along a plane perpendicular to the axis 340 of the sample container 100. For example, for the "free-floating" float 710, the separation of the liquid sample 420 into a stratification of components would result in the collection of one or more components that have similar specific gravity to that of the float 710. In one embodiment, with the float 710, the collection region 720 for the one or more components is located close to the container wall (e.g., the surface section 450 and/or the surface section 550). In another embodiment, the collection region 720 should be amenable to acoustic droplet ejection from the sample container 100. For example, the collection region corresponds to an acoustic path that is uniform even if the acoustic generator 210 moves in the horizontal plane (e.g., in the "x direction" and/or in the "y direction"). In another example, the collection region corresponds to an acoustic path that traverses a flat section of the float 710. In yet another example, through such acoustic path, the acoustic energy (e.g., the acoustic beam 410) is focused to a focal point near the free surface of the one or more components in the collection region from which one or more droplets 430 can be emitted with a trajectory towards the outlet 220.

According to one embodiment, there may be more than one "free-floating" float 710 in the sample holder 100, and each float 710 has a different specific gravity adapted to capture a different collection of one or more components of the liquid sample 420. According to another embodiment, it is desirable to retain the collection of one or more components of the liquid sample 420 in the collection region 720 if the sample container 100 moves from the vertical orientation to the horizontal orientation.

For example, a depression within the float 710 is used to as the collection region 720 for retaining the one or more components collected therein during stratification. In another example, the cross-section of the float 710 substantially conforms to the cross-section of the sample container 100, even though the cross-section of the float 710 has the depression that is used for sample collection and retention, as shown in FIG. 7(A). In other examples, others geometries for the float 710 would suffice if the float 710 can retain the one or more components in the transition from the vertical orientation to the horizontal orientation, and would preferably also have features that make the float suitable for acoustic ejections of droplets.

In yet another example, the depression region of the float 710 for collecting one or more components is adapted to collect a different volume. In yet another example, the geometry of the collection region 720 of the float 710 can change in cross-section, but the collection region 720 should not be constructed as to obstruct movement of the liquid sample 420 and/or prevent stratification of the liquid sample 420 when the sample container 100 is in the vertical orientation.

FIG. 7(B) is a simplified diagram showing another cross-section of the float 710 used in the sample container 100 according to another embodiment of the present invention. This diagram is merely an example, which should not unduly limit the scope of the claims. One of ordinary skill in the art would recognize many variations, alternatives, and modifications.

As shown in FIG. 7(B), the float 710 includes multiple collection regions 720. For example, the multiple collection regions 720 have the same geometries and/or the same dimensions. In another example, the multiple collection regions have different geometries and/or different dimensions.

FIG. 8 is a simplified diagram showing one or more droplets of the liquid sample being ejected from the sample container 100 by the acoustic generator 210 to a target according to an embodiment of the present invention. This diagram is merely an example, which should not unduly limit the scope of the claims. One of ordinary skill in the art would recognize many variations, alternatives, and modifications.

As shown in FIG. 8, the sample container 100 (e.g., a sample tube) is placed in the horizontal orientation. In one embodiment, an acoustic beam (e.g., the acoustic beam 410) generated by the acoustic generator 210 enters the sample container 100 through the acoustic coupling material 240 and focuses near the meniscus of the liquid sample 420 within the sample container 100. In another embodiment, one or more droplets 430 of the liquid sample 420 are ejected by the acoustic beam out of the sample holder 100 through the outlet 220 towards a target 810, which is positioned above the outlet 220 of the sample holder 100.

According to some embodiments, the destination for the droplets 430 of the liquid sample 420 from the sample container 100 can be a variety of targets 810 held by a target holder that is in proximity to the outlet 220 of the sample container 100. For example, the target holder is a device onto which the target 810 can be clipped or otherwise temporarily attached. In another example, the target holder includes guides for the motion of the target 810 in the x direction and/or in the y direction, and/or includes a full x-y automated motion system (e.g., an "x-y stage"). In yet another example, the target 810 is a reservoir (e.g., a tube and/or a well of a well plate) or another sample container. In yet another example, the target 810 is a diagnostic receiver (e.g., a microfluidic device, an array, a test strip, a filter paper, and/or a dried blood spot (DBS) system).

According to certain embodiments, following one acoustic ejection of a droplet of the liquid sample 420, it may be desired to eject from the same sample container 100 to another position on the target 810 (e.g., to another well in the same well plate to hold an aliquot with which a different test will be carried out, and/or to a different test strip suitable for a different type of test). For example, the target 810 is then moved automatically under the control of the controller or manually by the user, optionally with the assistance of markings or stops on the target holder. According to some embodiments, after one or more acoustic ejections of the one or more droplets 430 have been carried out from one sample container 100, it may be desired to repeat the ejection operation from a different sample container 100 to the same target 810 or a different target. For example, one can simply remove the sample container 100 from the sample holder and repeats the process to eject from a new sample container 100.

Various kinds of sample containers 100 can be used, but sample collection tubes are preferred according to certain embodiments of the present invention. In one embodiment, tubes of the type called "micro tubes" (e.g., 1.3 mL) are employed. In another embodiment, the size of the sample container 100 is 10 mL, 1 mL, 300 µL, 100 µL, 10 µL, or 1 µL. According to some embodiments, it would be preferable to scale the droplet size used in the acoustic ejection process in accordance with the sample container 100. For example, the droplet size for a 1-mL sample container is 1 µL or larger.

In another example, the droplet size for a 100-μL sample container is 10 nL, 1 nL, or 10 pL.

According to one embodiment, a sample collection tube includes one or more flat bottoms and/or one or more flat sides. According to another embodiment, it is desired to avoid imperfections or non-uniformities at the center of the side surface, and avoid imperfections or non-uniformities at the bottom from the gate where the plastics entered the mold in which the sample collection tube has been formed.

In one embodiment, a sample collection tube that is used as a sample container 100 includes one or more flat bottoms. For example, the flat bottoms have no imperfections (e.g., gates) from the molding process. In another example, the flat bottoms can facilitate transfers of droplets of a liquid sample (e.g., ejections of droplets of the liquid sample 420) from the sample container 100 along the long axis (e.g., the axis 340) when the sample collection tube is in the vertical orientation. In another embodiment, a sample collection tube that is used as a sample container 100 includes one or more flat sides. For example, the sample collection tube is placed in the horizontal orientation, and the acoustic energy (e.g., the acoustic beam 410) is applied through the side of the sample container 100 and thus ejects a droplet of a liquid sample (e.g., the liquid sample 420) toward an opposing outlet (e.g., the outlet 220). In another example, when the sample collection tube is in the horizontal orientation, the acoustic path from the acoustic generator (e.g., the acoustic generator 210) to the liquid meniscus is relatively uniform even if the acoustic generator moves in the horizontal plane (e.g., in the "x direction" and/or in the "y direction"), and the acoustic path is unobstructed by bubbles or irregularities in the surface geometry. In yet another embodiment, a sample collection tube that is used as a sample container 100 includes both one or more flat bottoms and one or more flat sides. For example, the sample container 100 can be used for ejections of droplets when the sample container is oriented vertically and horizontally.

As discussed above and further emphasized here, FIGS. 2, 4(A), 4(B), 5(A), 6 and 8 are merely examples, which should not unduly limit the scope of the claims. One of ordinary skill in the art would recognize many variations, alternatives, and modifications. For example, the acoustic generator 210 is a part of an acoustic ejection system, which includes an acoustic focusing subsystem. In another example, the acoustic focusing subsystem has a fixed focal distance or a variable focal distance. According to one embodiment, the focusing subsystem with a fixed focal distance is used if cost reduction is important. According to another embodiment, the focusing subsystem includes one or more spherical acoustic lenses and/or one or more Fresnel lenses.

In one embodiment, there are certain advantages in having a relatively high focal distance, for example, one which results from an f/4 lens, for ejecting from high aspect ratio fluid layers as may be found in the sample container 100 in the vertical orientation. In another embodiment, relatively low focal distances with small F-number lenses are better suited for droplet ejections from the sample container 100 in the horizontal orientation. As to the frequency of the acoustic energy, if the volumes of droplets to be ejected range from about 2.5 nL to 5 μL or from 100 nL to 1 μL, the corresponding acoustic frequencies used for such ejections range from about 1 MHz to 15 MHz in linear chirp waveform according to some embodiments. According to certain embodiments, for small sample containers 100 and/or if the fluid layer is very thin, smaller droplets may be desirable, and droplets below 1 nL or below 100 pL in size are ejected by using higher acoustic frequency.

Additionally, a controller is coupled to the acoustic generator 210 and used for acoustic ejection and/or analysis according to certain embodiments. For example, the controller includes a computer and/or a similar microprocessor-based system, which executes software and/or firmware. In another example, the controller further includes one or more microprocessors designed specifically to perform algorithms of digital signal processing (DSP) and/or having particular advantages for the performance of such algorithms. In yet another example, such controller also includes communications hardware (e.g., a network interface) and corresponding software, to communicate with other laboratory automation equipment and/or computers. In yet another example, the controller also includes one or more screens (e.g., one or more LCD screens), and/or one or more input devices (e.g., a joystick, a keyboard, and/or in the form of touch capability on a screen). In yet another example, the acoustic ejection system possesses or be connected to automated handling equipment which may, for example, transport sample containers or targets.

According to some embodiments, one or more sample containers (e.g., one or more sample containers 100) and/or one or more targets (e.g., one or more targets 810) that are involved in ejection operations are marked with machine readable markings, such as bar codes. For example, the controller reads these markings using an appropriate sensor and causes the markings to be entered into a database or others in order to record the identities of the one or more sample containers and/or the one or more targets. In another example, the fact that one or more droplets (e.g., one or more droplets 430 of the liquid sample 420) have been ejected from a particular container (e.g., the sample container 100) to a particular target (e.g., the target 810) is recorded by typing at a console or using a separate bar code reader.

According to certain embodiments, mixing is desired in situations where liquid samples (e.g., biological samples) to be ejected include biological cells. For example, for blood samples, cells may have settled to the bottom of the sample container 100, so acoustic energy that is generated by the acoustic generator 210 can be used to get the cells moving into the bulk fluid. In another example, some relative motion of the acoustic beam (e.g., the acoustic beam 410) with respect to the sample container 100 is used to improve mixing of the samples. In one embodiment, such relative motion includes the sweep of the beam 410 upward in the fluid as the sample container 100 approaches the acoustic lens (e.g., as part of the acoustic focusing subsystem) and/or includes some lateral relative motion that gets the focus of the beam away from the center of the sample container 100. In another embodiment, for mixing, it is useful to impart momentum to the cells that have settled along the outer edge of the sample container 100.

According to some embodiments, the appropriate energy level of an acoustic beam (e.g., the acoustic beam 410) for droplet ejections is determined experimentally. U.S. Pat. No. 7,717,544 is incorporated by reference herein for all purposes. In one embodiment, such determination of the appropriate energy level includes some or all of the following processes:

a) obtaining from past data a scaled-back waveform at a relatively low energy level which is reasonably expected not to be sufficient to eject a droplet.

b) directing the acoustic generator (e.g., the acoustic generator 210) to generate the scaled-back waveform and focusing the generated waveform to a location somewhat below the top surface of the fluid (e.g., the liquid sample 420).

c) some time thereafter (e.g., a few hundred microseconds thereafter), sending an interrogation pulse to the top surface of the fluid. For example, the interrogation pulse is brief (e.g., lasting only one or two cycles), and/or is at the center frequency of the acoustic transducer (e.g., used as the acoustic generator 210). In another example, the interrogation pulse has sufficiently low power so as not to significantly perturb further the top surface of the fluid (e.g., the liquid sample 420).

d) optionally, isolating the echo from the interrogation pulse by filtering or otherwise isolating the echo from other inputs sensed by the transceiver.

e) subjecting the echo to a Fourier-type transform algorithm (e.g., a Fast Fourier Transform (FFT)). For example, a Fourier-type transform algorithm is any algorithm which reaches a result that can be calculated by a technique that includes a step of performing or approximating a discrete or continuous convolution of the sample data with a complex exponential function of a discrete or continuous variable. In another example, the Fourier-type transform algorithm includes the Discrete Fourier Transform (DFT).

As shown in FIGS. 1(A), 1(B), 2, 3, 4(A), 4(B), 5(A), 5(B), 6, 7(A), 7(B), and/or 8, the sample container 100 includes one or more interior surfaces (e.g., one or more internal walls) and/or other components integral to the interior of the container 100, and such interior surfaces and/or components can be in direct contact with the liquid sample (e.g., the liquid sample 420) after the liquid sample enters the sample container 100. For example, the one or more interior surfaces and/or other components integral to the interior of the container 100 are modified to facilitate the attachment of one or more chemical materials and/or one or more biological materials, and such one or more chemical materials and/or one or more biological materials are used to preserve one or more components of the liquid sample (e.g., the liquid sample 420) from degradation.

FIG. 9 is a simplified diagram showing various combinations of surface treatment processes for one or more interior surfaces of the sample container 100 and/or one or more other components integral to the interior of the container 100 according to certain embodiments of the present invention. This diagram is merely an example, which should not unduly limit the scope of the claims. One of ordinary skill in the art would recognize many variations, alternatives, and modifications.

For example, FIG. 9 shows all the ligands are linked via one or more amino groups, but the linking can be accomplished also with one or more sulfhydryl groups and/or hydrazines, aldehydes, carboxylic acids, dienophiles, dienes, and/or alkynes. One of ordinary skill in the art would recognize these ligand linkage alternatives as well as other variations, alternatives, and modifications. In another example, the symbol "●" as shown in FIG. 9 represents a ligand.

In yet another example, the one or more components integral to the interior of the sample container 100 includes the inlet 110 and/or the cap 120. In yet another example, the surface and/or other component in FIG. 9 are comprised of at least one or more materials that are different from polypropylene. In one embodiment, the one or more materials include a glass. In another embodiment, the one or more materials include a polymer (e.g., polyethylene, polystyrene, polycarbonate, and/or COC) that is different from polypropylene.

As shown in FIG. 9, according to certain embodiments, one or more interior polypropylene surfaces of the sample container 100 and/or other polypropylene components integral to the interior of the container 100 are first modified with one or more of processes 1, 2, 3, 4, and/or 5.

Process 1: plasma treatment with an active alcohol is performed. For example, the one or more interior polypropylene surfaces of the sample container 100 are treated with a plasma in the presence of a suitable hydroxyl donator (e.g., allyl alcohol or another reactive alcohol) to yield one or more corresponding surfaces which are marked by the addition of covalently-bound hydroxyl groups.

Process 2: chemical oxidation is performed with or without some oxo- and carboxy-moieties being present. For example, the one or more interior polypropylene surfaces of the sample container 100 are chemically oxidized by treatment with a strong oxidant (e.g., persulfate or other oxidative compounds) in order to form one or more corresponding surfaces modified by the presence of hydroxyl, aldehydic, ketonic and/or carboxylic acid groups.

Process 3: plasma treatment with an active amine is performed. For example, the one or more interior polypropylene surfaces of the sample container 100 are treated with a plasma in the presence of an active amine donator (e.g., allyl amine or other reactive amine) to form covalently linked amines moieties on the surfaces.

Process 4: atomic layer deposition (such as alumina or silica) is performed. For example, the one or more interior polypropylene surfaces of the sample container 100 are chemically modified through atomic layer deposition to place one or more thin coating layers of oxide (e.g., silica or alumina) onto the surfaces that would be exposed to the liquid sample (e.g., the liquid sample 420). In another example, the one or more thin coating layers of oxide provide silyl alcohol or aluminum hydroxyl groups for further derivitization.

Process 5: photocrosslinked hydrophilic polymer is performed with or without N-hydroxysuccinimide (NHS) modifications. For example, the one or more interior polypropylene surfaces of the sample container 100 are photocrosslinked to an amine-reactive, hydrophilic polymer according to yet another embodiment. In another example, such surface chemistry involves, for covalent immobilization, one or more coating layers of protein molecules, peptides, or other amine-bearing molecules. In yet another example, the surface chemistry involves an N-oxysuccinimide (NHS ester) or an epoxide. In yet another example, deposition of photocrosslinked hydrophilic polymer with reactive groups is performed.

Also as shown in FIG. 9, according to some embodiments, after the one or more interior polypropylene surfaces of the sample container 100 and/or other polypropylene components integral to the interior of the container 100 are first modified with the processes 1, 2, 3, 4, and/or 5, the one or more interior polypropylene surfaces of the sample container 100 and/or other polypropylene components integral to the interior of the container 100 are further modified with one or more of processes 6, 7, and/or 8.

Process 6: silylation is performed. For example, the silylation process yields one or more interior surfaces with exposed amines and/or epoxy groups. In another example, the silylation process yields one or more interior surfaces with exposed hydrazines, aldehydes, carboxylic acids, dienophiles, dienes, alkynes, sulfides and/or other chemical moieties to create covalent linkages between chemical entities.

Process 7: one or more homobifunctional linkers (e.g., one or more amino-active homobifunctional linkers) are used. For example, the one or more homobifunctional linkers are selected specifically to link to free amines and/or to other chemically active moieties. In another example, one or more heterobifunctional linkers, instead of one or more homobifunctional linkers, are used if the binding moiety of the surface is different from the binding moiety of the one or more ligands.

Process 8: one or more ligands are added. For example, these ligands actively bind to or inhibit the activity of endogenous degradative enzymes in the liquid sample. In another example, these ligands also impact the non-specific binding of materials in the liquid sample by affecting one or more properties of the one or more interior surfaces of the sample container.

In one embodiment, the one or more interior surfaces that have been treated by plasma with active amine can further react with an excess of a homo-bifunctional amine-reactive linker. For example, this linker includes, without limitation, p-phenylene diisothiocyanate, bis(polyethylene glycol bis [imidazoyl carbonyl]), bis[2-(N-succinimidyl-oxycarbonyloxy)ethyl]sulfone, 4,4'-diisothiocyanatostilbene-2,2'-disulfonic acid, dimethyl pimelimidate, ethylene glycol-bis (succinic acid N-hydroxysuccinimide ester), sebacic acid bis(N-succinimidyl)ester, suberic acid bis(N-hydroxysuccinimide ester), sulfodisuccinimidyl tartrate, disuccinimidyl tartrate, bis(succinimidyl)penta(ethylene glycol) (BS5), bis (succinimidyl)nona(ethylene glycol) (BS9), and/or suberic acid bis(3-sulfo-N-hydroxysuccinimide ester). In another example, the chemical reaction on the one or more interior surfaces are accelerated or improved in yield if a carbodiimide (e.g., N,N'-dicyclohexylcarbodiimide and/or N-(3-dimethylaminopropyl)-N'-ethylcarbodiimide) is added. In yet another example, a primary amine on the modified one or more interior surfaces is derivatized in a manner that allows the surfaces to be further modified with the addition of an amino-containing ligand.

In another embodiment, the one or more interior surfaces that have been treated by plasma with active amine are further treated with glutaraldehyde as a precursor step to forming one or more glutaraldehyde networks.

In yet another embodiment, the one or more interior surfaces that have been treated with plasma with active alcohol are silylated with 3-aminopropyl trimethoxysilane (APTMS) and/or a related (aminoalkyl)(trialkoxy)silane (e.g., 4-aminobutyltriethoxysilane (ABTES) and/or 11-aminoundecyltriethoxysilane). For example, such silylation process provides hydrolytic stability to the derivatized interior surfaces. In another example, the free amine groups linked to the surfaces are treated with a homobifunctional reagent in preparation to binding a ligand that bears a primary amine. In yet another embodiment, the one or more interior surfaces that have been treated by plasma with active alcohol are silylated with one or more reagents, such as (3-glycidoxypropyl)trimethoxysilane or 5,6-epoxyhexyltriethoxysilane. For example, such silylated interior surfaces are modified with an epoxy moiety that can react with a nucleophile to form a covalently linked attachment to a ligand. In yet another embodiment, the one or more interior surfaces that have been treated by plasma with active alcohol are silylated with 11-(succinimidoyloxy)undecyldimethylethoxysilane. For example, such silylated interior surfaces can react with the primary amine of a ligand to form a covalent bond. In another example, this reaction with the primary amine are accelerated or improved in yield if a carbodiimide (e.g., N,N'-dicyclohexylcarbodiimide or N-(3-dimethylaminopropyl)-N'-ethylcarbodiimide) is added.

As described above, for the sample container 100, the one or more interior surfaces have been modified so that an amine-reactive linker is exposed and available to link to a free amine of a ligand according to certain embodiments. In one embodiment, the free amine is a functional group on the molecule 4-(2-aminoethyl)benzenesulfonyl fluoride (AEBSF), and treating the silylated one or more interior surfaces with AEBSF can link a known suicide inhibitor of serine proteases to the one or more interior surfaces.

In another embodiment, the derivatized one or more interior surfaces are linked to the primary amino group of the ligand, N-alpha-tosyl-L-lysine chloromethyl ketone (TLCK), which is a known irreversible inhibitor of the protease bromelain and other sulfhydryl proteases. For example, treating the activated one or more interior surfaces with TLCK can immobilize the inhibitor but leaves the active chloromethyl ketone site accessible to proteases in the solution.

In yet another embodiment, the activated one or more interior surfaces react with the ligand serum $\alpha_1$-antitrypsin (e.g., A1AT). For example, A1AT is a 52 kDa protein that can bind tightly to trypsin, chymotrypsin and other proteases and thus effectively remove them from the liquid sample and eliminate their degradative effects on peptide biomarkers.

In yet another embodiment, the amine groups of ligand trypsin inhibitor proteins that have been isolated from lima beans (i.e., *Phaseolus lunatus*), bovine pancreas, chicken egg whites and/or soybeans (i.e., *Gycine max*) are linked, via activated surface groups, to the one or more interior surfaces. For example, all these proteins can bind to trypsin and related proteins in a way similar to that seen with A1AT.

In yet another embodiment, the ligands are affinity reagents including, without limitation, aptamers, antibodies, antibody fragments, and/or antibody mimetics that have free amino groups and/or other functional moieties naturally present and/or added. For example, the functional moieties can be used to covalently link them to the activated one or more interior surfaces. In another example, aptamers are selected specifically because of their high affinity for serine, sulfhydryl, and/or metalloproteinases, and the aptamers are attached to the one or more interior surfaces in order to reduce the effective concentration of those proteinases in the liquid sample.

In yet another embodiment, the amino-reactive one or more interior surfaces react with the ligand 2-aminomethyl-18-crown-6 (1,4,7,10,13,16-hexaoxacyclooctadecan-2-ylmethanamine). For example, the 18-crown-6 moiety of the structure is a very strong binder of calcium and/or other polyvalent cations. In another example, binding this structure to the one or more interior surfaces can remove calcium from solution and inhibit the activity of metalloproteases.

In yet another embodiment, the ligand that can react with the amino-reactive one or more interior surfaces is one of other primary amine-containing chelators of calcium and/or other polyvalent cations including, but not limited to N-alpha-N-alpha-bis(carboxymethyl)-L-lysine((2S)-6-amino-2-[bis(carboxymethyl)amino]hexanoic acid), aminobenzyl-EDTA, 1,8-diamino-3,6,10,13,16,19-hexaazabicyclo[6.6.6]-eicosine, 5-S-(4-aminobenzyl)-1-oxa-4,7,10-triazacyclododecane-4,7,10-tris(acetic acid), S-2-(4-aminobenzyl)-1,4,7-triazacyclononane-1,4,7-triacetic acid, 3,6,9,15-tetraazabicyclo[9.3.1]-pentadeca-1(15),11,13-triene-4-(S)-(4-aminobenzyl)-3,6,9-triacetic acid, 2-(4-aminobenzyl)-diethylenetriaminepenta(t-butyl acetate), and/or 2-(4-aminobenzyl)-1,4,7,10-tetraazacyclododecane-1,4,7,10-tetraacetic acid.

According to another embodiment, the effective surface area of the one or more interior surfaces is increased by one or more physical modifications to the geometry of the one or more surfaces. For example, the physical modifications include adding fins, roughness and/or pores. In another example, the physical modifications include increasing the number of binding sites through one or more chemical processes that do not significantly displace the sample volume. As described above, for the sample container 100, the ligand or ligands that are ultimately attached to the one or more interior surfaces should bind to one or more materials that are endogenous in the liquid sample and that would lead to the degradation of other components in the liquid sample, according to some embodiments. For example, irreversible protease inhibitors (e.g., TLCK and/or AEBSF) can bind proteases in the blood and stop their biological activity, and thus help maintain the concentration and integrity of proteins and/or peptides in the blood sample, where these proteins and/or peptides can serve as biological markers or determinants of biological functions. In another example, if a metal chelator (e.g., 2-aminomethyl-18-crown-6) is bound to the one or more interior surfaces, cations such as calcium are depleted from the solution. Such depletion can reduce or prevent the activity of metalloproteases and can also reduce the tendency for the blood sample to coagulate. In both examples as described above, aliquots of liquid sample that are transferred from the sample container 100 for analysis do not contain the immobilized inhibitor according to certain embodiments. For example, the aliquots of liquid sample are free from contaminations that may preclude the use of specific tests that could be affected by the presence of free protease inhibitor and/or metal chelator. In yet another embodiment, the homobifunctional linker arm can be replaced with homopolyfunctional linker arm, such as poly(N-hydroxysuccinimide methacrylate) and/or a heteropolyfunctional linker arm. For example, a homopolyfunctional linker is expanded through dendrimer generation growth to provide a plurality of binding sites for materials in the liquid sample with a single attachment point to the one or more interior surfaces. In another example, such replacement of the homobifunctional linker arm by a homopolyfunctional linker arm allows the attachment of a higher density of ligands to the one or more interior surfaces than can be afforded with a bifunctional linker. In yet another example, such replacement of the homobifunctional linker arm by a homopolyfunctional linker arm allows more of a predetermined material to be removed from the liquid sample because the number of binding sites provided by the branched and/or multi-site linkers can exceed that of bifunctional linkers.

According to another embodiment, a method for collecting a liquid sample in a sample container is provided. For example, the sample container is adapted to holding the liquid sample, and optionally to enabling separation of the sample into components. In another example, the sample container (e.g., the sample container 100) is further adapted for acoustic ejection of droplets both from the inlet 110 through which the liquid sample has been introduced into the sample container, as well as from other positions (e.g., the outlet 220) that offer better acoustic paths or access to separated components.

According to another embodiment, the sample container (e.g., the sample container 100) is adapted to providing access to the acoustic ejector (e.g., the acoustic generator 210). For example, the acoustic ejector sends one or more interrogation pulses towards the sample container. Based on the interrogation pulses, the controller can determine location of the sample container, parts of the sample container, nature of the liquid sample therein, and/or properties and/or locations of separated components within the liquid sample. In another example, the position of the acoustic ejector can be adjusted based on such determined information in order to place focus of the acoustic energy near a free surface of the liquid sample or sample components where a droplet can be ejected. In yet another example, optionally, the acoustic ejector can be positioned to apply acoustic energy to mix components of a biological sample in order to form a more homogeneous sample within the closed or open sample container 100.

According to yet another embodiment, the sample container (e.g., the sample container 100) is adapted to preserve the liquid sample (e.g., the liquid sample 420) by providing one or more treated interior surfaces and/or other treated components integral to the interior of the sample container (e.g., the inlet 110 and/or the cap 120 of the sample container 100), in order to reduce the rate of degradation of liquid sample that has been introduced to the sample container. For example, in the liquid sample, substances that can lead to sample degradation are immobilized and/or deactivated by one or more treatments of the one or more interior surfaces; therefore, such treatments can preserve composition of the liquid sample for desired analytical tests. In another example, the one or more treatments of the one or more interior surfaces are initiated by contact of the liquid sample with the one or more interior surfaces of the container, and the treatments are also compatible with acoustic ejection of droplets from the sample container. In yet another example, the treatments do not contaminate any droplets (e.g., the one or more droplets 430) ejected from the sample container (e.g., the sample container 100), and such treatments also occurs with sufficient abundance to provide substantially the same preservative effect for the range of volumes of liquid sample which can be placed in the sample container.

There are a wide range of applications for various embodiments of the present invention in the handling of biological samples. In one embodiment, many patient samples containing cells are used to seed cell cultures and are employed to determine the presence of one or more pathogenic materials such as bacteria and/or viruses. For example, one or more sample containers (e.g., the sample container 100) having an interior surface that is coated with a layer of solid or semisolid medium within which cells are grown are inoculated with the desired type of cells. In another example, after the cells are subjected to conditions appropriate for cultivation, the cells are removed from the sample containers as a suspension within the ejected droplets (e.g., the one or more droplets 430) and may optionally be concentrated. In yet another example, afterwards, if desired, certain viral matter is extracted from the cells.

According to another embodiment, a sample container for holding and transferring a liquid sample includes an inlet configured to allow a liquid sample to enter a sample container, and an outlet configured to allow one or more droplets of the liquid sample to exit the sample container by one or more acoustic ejections respectively. The inlet and the outlet are in different locations. For example, the sample container is implemented according to at least FIGS. 1(A), 1(B), 2, 3, 4(A), 4(B), 5(A), 5(B), 6, 7(A), 7(B), and/or 8.

In another example, the sample container further includes a side surface configured to allow acoustic coupling between the sample container and an acoustic generator and allow focusing of an acoustic beam to a focal point within the liquid sample. In yet another example, the sample container is further configured to allow the one or more acoustic ejections of the one or more droplets through the outlet if the side surface is placed in the horizontal orientation. In yet another example, the outlet is opposite to the side surface. In yet another example, the outlet is controlled by at least one selected from a group consisting of a cap, a septum, a sliding component, a twisting component, an adhesive material, and an electrically-activated component.

In yet another example, the sample container further includes one or more floats being associated with one or more densities corresponding to one or more components of the liquid sample. In yet another example, the one or more floats are acoustically uniform. In yet another example, the one or more floats are associated with one or more acoustic impedance values that are different from ones for the one or more components of the liquid sample respectively. In yet another example, the sample container is further configured to be modified by adding one or more materials into the liquid sample to cause one or more chemical reactions and to reduce degradation or decomposition of one or more analytes in the liquid sample. In yet another example, the sample container is further configured to trap or inactivate one or more components of the liquid sample by the one or more chemical reactions. In yet another example, the sample container is further configured to prevent releasing any of the one or more materials into the one or more ejected droplets.

According to yet another embodiment, a method for holding and transferring a liquid sample includes transferring a liquid sample into a sample container through an inlet, and acoustically ejecting one or more droplets of the liquid sample out of the sample container through an outlet. The inlet and the outlet are in different locations. For example, the method is implemented according to at least FIGS. 1(A), 1(B), 2, 3, 4(A), 4(B), 5(A), 5(B), 6, 7(A), 7(B), and/or 8.

In another example, the method further includes placing a side surface of the sample container in the horizontal orientation, acoustically coupling the sample container and an acoustic generator through at least the side surface, generating an acoustic beam by the acoustic generator, and focusing the acoustic beam to a focal point within the liquid sample. In yet another example, the process for acoustically ejecting one or more droplets of the liquid sample out of the sample container through an outlet includes acoustically ejecting the one or more droplets through the outlet opposite to the side surface. In yet another example, the method further includes removing one or more bubbles from the liquid sample by at least rocking or rolling the sample container. In yet another example, the method further includes detecting by acoustics one or more bubbles within the liquid sample, and removing the one or more bubbles from the liquid sample.

In yet another example, the method further includes placing one or more floats into the sample container, and stratifying the fluid sample into a plurality of components. Each of the one or more floats is associated with a density corresponding to one or more components of the plurality of components. In yet another example, the method further includes changing the sample container from the vertical orientation to the horizontal orientation with each of the one or more floats keeping the one or more components of the plurality of components in a selected collection region. In yet another example, the method further includes determining acoustically a location of at least one of the one or more floats. The process for acoustically ejecting one or more droplets of the liquid sample out of the sample container through an outlet includes acoustically ejecting at least one droplet from the one or more components corresponding to the at least one of the one or more floats.

In yet another example, the method further includes modifying the sample container by adding one or more materials into the liquid sample to cause one or more chemical reactions and to reduce degradation or decomposition of one or more analytes in the liquid sample. In yet another example, the process for modifying the sample container includes trapping or inactivating one or more components of the liquid sample. In yet another example, the process for modifying the sample container does not release any of the one or more materials into the one or more ejected droplets.

In yet another example, the method further includes placing a side surface of the sample container in the horizontal orientation, and determining one or more locations of one or more floats respectively, the one or more floats being within the sample container. In yet another example, the process for determining one or more locations of one or more floats respectively includes detecting the one or more floats acoustically. In yet another example, the method further includes acoustically coupling the sample container and an acoustic generator through at least the side surface, aligning the acoustic generator with at least one of the one or more floats based on at least information associated with one of the one or more locations, generating an acoustic beam by the acoustic generator, and focusing the acoustic beam to a focal point corresponding to the one of the one or more floats within the liquid sample.

According to yet another embodiment, a method for holding a liquid sample includes transferring a liquid sample into a sample container, adding one or more materials to one or more interior surfaces of the sample container, and binding one or more components of the liquid sample to the one or more materials on the one or more interior surfaces of the sample container. For example, the method is implemented according to at least FIG. 9.

In another example, the process for binding one or more components of the liquid sample to the one or more materials on the one or more interior surfaces of the sample container includes binding one or more moieties of one or more predetermined types within the liquid sample to the one or more interior surfaces through the one or more materials. In yet another example, the process for binding one or more moieties of one or more predetermined types within the liquid sample to the one or more interior surfaces through the one or more materials includes binding 50% or more of the total amount of the one or more moieties of the one or more predetermined types within the liquid sample to the one or more interior surfaces through the one or more materials. In yet another example, binding capacity of one of the one or more materials exceeds 50% of a predetermined amount of the one or more moieties within the liquid sample. In yet another example, the process for binding one or more moieties of one or more predetermined types within the liquid sample to the one or more interior surfaces through the one or more materials includes providing, by one linker of the one or more materials, a first number of attachment positions for the one or more components in the liquid sample. The first number of attachment positions is larger than a second number of attachment points provided by the one linker to the one or more interior surfaces. In yet another example, the one linker includes one selected from a group consisting of a homopolyfunctional linker and a heteropolyfunctional linker.

In yet another example, the maximum volume of the liquid sample allowed by the sample container is 1 mL or less. In yet another example, the maximum volume of the liquid sample allowed by the sample container is 300 µL or less. In yet another example, the method further includes transferring one or more droplets of the liquid sample out of the sample container. The one or more transferred-out droplets do not include any of the one or more materials. In yet another example, the process for binding one or more components of the liquid sample to the one or more materials on the one or more interior surfaces of the sample container includes reducing degradation or decomposition of one or more moieties in the liquid sample.

Example A for Derivatization of Sample Container

Example A was performed as an embodiment as shown in FIG. 9. Polypropylene 1.5 mL microfuge tubes (Eppendorf, Safe-Lock, catalog number 022363204, Hauppauge, N.Y.) were delivered to PVA TePla America (Corona, Calif.) where these tubes were treated with a plasma to make the exposed surfaces of the tubes hydrophilic through the introduction of covalently-bound hydroxyl groups.

Afterwards, for these plasma-treated tubes, their internal surfaces were silylated. Two (2) mL of neat 3-aminopropyltrimethoxysilane (APTMS, catalog number SIA0611.0, Gelest, Inc., Morrisville, Pa.) were added to 190 mL methanol and mixed to homogeneity. Ten (10) mL deionized water were added to the alcohol solution and the solution was mixed to homogeneity. The solution was allowed to stand at room temperature for one hour with occasional mixing, so that the silylating reagent can be hydrolyzed and form oligomers. The plasma-treated polypropylene tubes were filled with the APTMS solution, capped and gently shaken overnight.

After overnight incubation, the liquid was poured from the tubes and the tubes were washed three times with 1.5 mL methanol, followed by two washes with isopropanol (EMD Millipore, catalog number PX1834-1, Darmstadt, Germany). The tubes were dried under vacuum. After being fully dried and cured, the tubes were stored closed, under a cover of nitrogen in the presence of desiccant packs (Thermo Fisher Scientific, catalog number 07-580, Waltham, Mass.) to ensure a dry, oxygen-free environment.

Immediately before the next step, solutions of three different ligands were prepared. A 50 mM Ligand AP solution was made by dissolving and thoroughly mixing 77 μL of 3-amino-1-propanol (AP, Sigma-Aldrich, catalog number A76400, St. Louis, Mo.) in 20 mL anhydrous dimethylformamide (DMF, Sigma-Aldrich, catalog number 227056). For example, solutions of AP are not expected to be inhibitors of trypsin proteolytic activity. A 5 mM Ligand TLCK solution was made by dissolving and thoroughly mixing 37 mg of N-alpha-tosyl-L-lysine chloromethyl ketone hydrochloride (TLCK, Sigma-Aldrich, catalog number 90182, Sigma-Aldrich, St. Louis, Mo.) into 20 mL anhydrous DMF. In another example, solutions of TLCK are expected to be inhibitors of trypsin proteolytic activity. A 5 mM Ligand AEBSF solution was made by dissolving and thoroughly mixing 24 mg of 4-(2-aminoethyl)benzenesulfonyl fluoride hydrochloride (AEBSF, catalog number A8456, Sigma-Aldrich) in 20 mL anhydrous DMF. In yet another example, solutions of AEBSF are expected to be inhibitors of trypsin proteolytic activity.

A solution of the homobifunctional linker di-(N-hydroxysuccinimidyl)-4,7,10,13,16-pentaoxanonadeca-1,19-dioate (BS5, Thermo Fisher Scientific Inc., catalog number 21581) was freshly prepared by dissolving 50 mg of the liquid in 20 mL of anhydrous DMF to make a solution of 4.7 mM. 11.3 μL of anhydrous pyridine (1.5 equivalents) was added to the DMF solution. One (1.0) mL of this solution was added to each of the cured APTMS-derivatized polypropylene tubes. The tubes were capped and incubated with occasional mixing for 2 hours at room temperature. The solution of BS5 was subsequently poured from the tubes.

One (1.0) mL of each of the three freshly prepared ligand solutions, including the Ligand AP solution, the Ligand TLCK solution, and the Ligand AEBSF solution, was immediately added to each freshly derivatized polypropylene tube and incubated at room temperature for 2 hours with occasional mixing. After incubation, the ligand solutions were poured from the tubes and the tubes were washed with 1.5 mL anhydrous DMF. A solution of 1.5 mL of 100 mM tris(hydroxymethyl)aminomethane (TRIS, Gibco-BRL, catalog number 15567-027, Grand Island, N.Y.) in water at pH 7.5 was added to each polypropylene tube. The tubes were incubated with the TRIS solution for 30 minutes at room temperature. This incubation was performed to ensure that there are no more active linker moieties attached to the internal walls of the tubes. The TRIS solution was discarded from the tubes and the tubes were washed three times with 1.5 mL deionized water. The tubes were then washed with 1.5 mL isopropanol and dried under a vacuum of 25 mm Hg at room temperature. After the tubes were completely dried, they were stored under nitrogen at 4° C.

Protease activity and the inhibition thereof were measured with a Fluorescent Protease Assay Kit (Thermo Scientific Pierce, catalog number 23266). TRIS-buffered saline (TBS, 25 mM Tris, 0.15 M NaCl, pH 7.2) was reconstituted from dry solids in the kit with deionized water. Trypsin stock solution was freshly prepared by dissolving TPCK trypsin from kit with 1 mL deionized water to make a 50 mg/mL solution. TPCK trypsin is treated with L-1-tosylamido-2-phenylethyl chloromethyl ketone (TPCK) to inhibit contaminating chymotrypsin activity without affecting trypsin activity. Aliquots of 10 μL were stored at −60° C. Individual aliquots of the stock solution were diluted in 1.0 mL of TBS (0.5 mg/mL), and 10 μL of this solution was further diluted in 10 mL of TBS (0.5 μg/mL). This solution was serially diluted 1:1 with TBS to create a trypsin solution of 62.5 ng/mL. The trypsin solution was kept in an ice bath until use. 200 μL of the diluted trypsin (12.5 ng) was added to each prepared polypropylene tube. The solution was aspirated and re-dispensed three times in each tube to assure complete mixing and contact of the solution with the derivatized internal walls of the tubes. A new disposable tip was used for each transfer. After incubation at room temperature for 120 minutes, 100 μL of the trypsin solution from each tube was placed into individual wells of a 96-well, black, flat-bottomed plate (Greiner Bio-one, catalog number 655076, Monroe, N.C.). FTC-casein (casein protein modified by the addition of fluorescein isothiocyanate, a part of the Fluorescent Protease Assay Kit) solution in TBS buffer was freshly prepared and 100 μL of this solution was added to each well and mixed via aspiration and dispense. The plate was incubated at room temperature for 95 minutes. The fluorescence of the samples in the 96-well plate was measured on a SpectraFluor Plus fluorescence spectrometer (Tecan, Männedorf, Switzerland) 5 minutes after the solution was added and additionally after 10, 20, 40, 60 and 95 minutes. Increased fluorescence is indicative of trypsin-mediated digestion of the added FTC-casein solution via the decrease of FRET-based fluorescence quenching that exists in the intact protein.

Control wells containing FTC-casein and no trypsin averaged a background fluorescence of 5382 RFU (relative fluorescence units) after 20 minutes. This value compared favorably to wells that contained FTC-casein, trypsin and 0.1 mM TLCK (6841 RFU) and FTC-casein, trypsin and 1.0 mM AEBSF (5265 RFU). 5382 RFU was subtracted from all values as the background fluorescence of the system. The average reading of wells that contained trypsin exposed to tubes with immobilized AP Ligand was 21289 RFU. For example, the AP Ligand is not expected to exhibit any inhibition of trypsin. In another example, 21289 RFU compared favorably to wells where a large amount of trypsin (50 ng/well) was present without any added inhibitor (21035 RFU). In both of these cases, one may expect significant trypsin activity without inhibition.

The trypsin that had been exposed to AEBSF Ligand immobilized as described above showed an average fluorescence of 13164 RFU, and the trypsin that had been exposed to TLCK Ligand immobilized as described above had a fluorescence of 15521 RFU. The AEBSF Ligand, immobilized as described above, showed 50% inhibition of trypsin activity, and the TLCK Ligand, immobilized as described above, showed 35% inhibition of trypsin activity. Hence the stronger inhibition of trypsin by immobilized ligands was achieved with AEBSF instead of TLCK. Furthermore, this method of inhibition is more effective if the tubes were initially plasma treated to yield a hydroxylated surface.

Example B for Derivatization of Sample Container

Example B was performed as another embodiment as shown in FIG. 9. Polypropylene 1.5 mL microfuge tubes were delivered to Integrated Surface Technologies (Menlo Park, Calif.) where they were treated to make the exposed surfaces of the tubes hydrophilic through atomic layer deposition of silica.

Afterwards, for these treated tubes, their internal surfaces were silylated. Two (2) mL of neat (3-glycidoxypropyl) trimethoxysilane (catalog number SIG5840.0, Gelest, Inc., Morrisville, Pa.) were added to 190 mL methanol and mixed to homogeneity. Ten (10) mL deionized water were added to the alcohol solution and the solution was mixed to homogeneity. The solution was allowed to stand at room temperature for one hour with occasional mixing, so that the silylating reagent can be hydrolyzed and form oligomers. The treated polypropylene tubes were filled with the silylating solution, capped and gently shaken overnight.

After overnight incubation, the liquid was poured from the tubes and the tubes were washed three times with 1.5 mL methanol, followed by two washes with isopropanol (EMD Millipore, catalog number PX1834-1, Darmstadt, Germany). The tubes were dried under vacuum. After being fully dried and cured, the tubes were stored closed, under a cover of nitrogen in the presence of desiccant packs (Thermo Fisher Scientific, catalog number 07-580, Waltham, Mass.) to ensure a dry, oxygen-free environment.

Immediately before the next step, solutions of three different ligands were prepared. A 50 mM Ligand AP solution was made by dissolving and thoroughly mixing 77 µL of 3-amino-1-propanol in 20 mL anhydrous dimethylformamide (DMF, Sigma-Aldrich, catalog number 227056). For example, solutions of AP are not anticipated to be inhibitors of trypsin proteolytic activity. A 5 mM Ligand TLCK solution was made by dissolving and thoroughly mixing 37 mg of N-alpha-tosyl-L-lysine chloromethyl ketone hydrochloride (TLCK, Sigma-Aldrich, catalog number 90182, Sigma-Aldrich, St. Louis, Mo.) into 20 mL anhydrous DMF. In another example, solutions of TLCK are expected to be inhibitors of trypsin proteolytic activity. A 5 mM Ligand AEBSF solution was made by dissolving and thoroughly mixing 24 mg of 4-(2-aminoethyl)benzenesulfonyl fluoride hydrochloride (AEBSF, catalog number A8456, Sigma-Aldrich) in 20 mL anhydrous DMF. In yet another example, solutions of AEBSF are expected to be inhibitors of trypsin proteolytic activity.

One (1.0) mL of each of the three freshly prepared ligand solutions, including the Ligand AP solution, the Ligand TLCK solution, and the Ligand AEBSF solution, was immediately added to each derivatized polypropylene tube and incubated at room temperature for 2 hours with occasional mixing. After incubation, the ligand solutions were poured from the tubes and the tubes were washed with 1.5 mL anhydrous DMF. A solution of 1.5 mL of 100 mM tris (hydroxymethyl)aminomethane (TRIS, Gibco-BRL, catalog number 15567-027, Grand Island, N.Y.) in water at pH 7.5 was added to each polypropylene tube. The tubes were incubated with the TRIS solution for 30 minutes at room temperature. This incubation was performed to ensure that there are no more active linker moieties attached to the internal walls of the tubes. The TRIS solution was discarded from the tubes and the tubes were washed three times with 1.5 mL deionized water. The tubes were then washed with 1.5 mL isopropanol and dried under a vacuum of 25 mm Hg at room temperature. After the tubes were completely dried, they were stored under nitrogen at 4° C.

Protease activity and the inhibition thereof were measured with a Fluorescent Protease Assay Kit (Thermo Scientific Pierce, catalog number 23266). TRIS-buffered saline (TBS, 25 mM Tris, 0.15 M NaCl, pH 7.2) was reconstituted from dry solids in the kit with deionized water. Trypsin stock solution was freshly prepared by dissolving TPCK trypsin from kit with 1 mL deionized water to make a 50 mg/mL solution. Aliquots of 10 µL were stored at −60° C. Individual aliquots of the stock solution were diluted in 1.0 mL of TBS (0.5 mg/mL), and 10 µL of this solution was further diluted in 10 mL of TBS (0.5 µg/mL). This solution was serially diluted 1:1 with TBS to create a trypsin solution of 62.5 ng/mL. The trypsin solution was kept in an ice bath until use. 200 µL of the diluted trypsin (12.5 ng) was added to each prepared polypropylene tube. The solution was aspirated and re-dispensed three times in each tube to assure complete mixing and contact of the solution with the derivatized internal walls of the tubes. A new disposable tip was used for each transfer. After incubation at room temperature for 120 minutes, 100 µL of the trypsin solution from each tube was placed into individual wells of a 96-well, black, flat-bottomed plate (Greiner Bio-one, catalog number 655076, Monroe, N.C.). FTC-casein—(casein protein modified by the addition of fluorescein isothiocyanate, a part of the Fluorescent Protease Assay Kit) solution in TBS buffer was freshly prepared and 100 µL of this solution was added to each well and mixed via aspiration and dispense. The plate was incubated at room temperature for 95 minutes. The fluorescence of the samples in the 96-well plate was measured on a SpectraFluor Plus fluorescence spectrometer (Tecan, Mannedorf, Switzerland) 5 minutes after the solution was added and additionally after 10, 20, 40, 60 and 95 minutes. Increased fluorescence is indicative of trypsinmediated digestion of the added FTC-casein solution via the decrease of FRET-based fluorescence quenching that exists in the intact protein.

Control wells containing FTC-casein and no trypsin averaged a background fluorescence of 5382 RFU (relative fluorescence units) after 20 minutes. This value compared favorably to wells that contained FTC-casein, trypsin and 0.1 mM TLCK (6841 RFU) and FTC-casein, trypsin and 1.0 mM AEBSF (5265 RFU). 5382 RFU was subtracted from all values as the background fluorescence of the system. The average reading of wells that contained trypsin exposed to tubes with immobilized AP Ligand was 20847 RFU. For example, the AP Ligand is not expected to exhibit any inhibition of trypsin.

The trypsin that had been exposed to AEBSF Ligand immobilized as described above showed an average fluorescence of 12592 RFU, and the TLCK Ligand immobilized as described above had a fluorescence of 13386 RFU. The AEBSF ligand, immobilized as described above, showed 53% inhibition of trypsin activity, and the TLCK Ligand, immobilized as described above, showed 48% inhibition of trypsin activity. Hence the stronger inhibition of trypsin by immobilized ligands was achieved with AEBSF instead of TLCK.

For example, some or all components of various embodiments of the present invention each are, individually and/or in combination with at least another component, implemented using one or more software components, one or more hardware components, and/or one or more combinations of software and hardware components. In another example, some or all components of various embodiments of the present invention each are, individually and/or in combination with at least another component, implemented in one or more circuits, such as one or more analog circuits and/or one or more digital circuits. In yet another example, various embodiments and/or examples of the present invention can be combined.

All patents, patent applications, and publications mentioned herein are hereby incorporated by reference in their entireties for all purposes. However, where a patent, patent application, or publication containing one or more express definitions is incorporated by reference, those express definitions should be understood to apply to the incorporated patent, patent application, or publication in which the one or more express definitions are found, but not to the remainder of the text of this application, in particular not to the claims of this application.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A method for selectively holding a first component of a liquid sample and selectively transferring a second component of the liquid sample relative to the first component, the method comprising:
    adding one or more materials to one or more interior surfaces of a sample container adapted for acoustic ejection;
    after adding the one or more materials to the one or more interior surfaces, transferring a liquid sample into the sample container, the liquid sample comprising the first component at a first concentration and the second component at a second concentration;
    binding the first component of the liquid sample to the one or more materials on the one or more interior surfaces of the sample container, the second component being unbound to the one or more materials on the one or more interior surfaces of the sample container;
    after the selective binding, acoustically ejecting out of the sample container a droplet comprising the second component; and
    reducing, by the acoustic ejecting, the second concentration of the second component within a portion of the liquid sample remaining within the sample container.

2. The method of claim 1 wherein the process for binding the first component of the liquid sample to the one or more materials on the one or more interior surfaces of the sample container includes binding one or more moieties of one or more predetermined types of the first component to the one or more interior surfaces through the one or more materials.

3. The method of claim 2 wherein the one or more materials includes a sufficient number of binding sites so as to bind 50% or more of the total amount of the one or more moieties of the one or more predetermined types of the first component to the one or more interior surfaces through the one or more materials.

4. The method of claim 2 wherein one of the one or more materials includes a sufficient number of binding sites so as to bind greater than 50% of a predetermined amount of the one or more moieties of the first component.

5. The method of claim 2 wherein the process for binding one or more moieties of one or more predetermined types of the first component to the one or more interior surfaces through the one or more materials includes providing, by one linker of the one or more materials, a first number of attachment positions for the first component of the liquid sample, the first number of attachment positions being larger than a second number of attachment points provided by the one linker to the one or more interior surfaces.

6. The method of claim 5 wherein the one linker includes one selected from a group consisting of a homopolyfunctional linker and a heteropolyfunctional linker.

7. The method of claim 1 wherein the maximum volume of the liquid sample allowed by the sample container is 1 mL or less.

8. The method of claim 7 wherein the maximum volume of the liquid sample allowed by the sample container is 300 µL or less.

9. The method of claim 1 wherein the process for binding the first component of the liquid sample to the one or more materials on the one or more interior surfaces of the sample container includes reducing degradation or decomposition of one or more moieties of the first component.

10. The method of claim 1, wherein the sample container comprises an inlet receiving the liquid sample and an outlet through which the droplet is acoustically ejected, wherein the inlet and the outlet are in different locations than one another.

11. The method of claim 10, wherein the sample container further includes a surface configured to be acoustically coupled to an acoustic generator that is movable relative to the sample container, and wherein the outlet is arranged opposite to the surface.

* * * * *